(12) United States Patent  
Shachar et al.

(10) Patent No.: US 9,109,029 B2  
(45) Date of Patent: Aug. 18, 2015

(54) COMPOSITIONS COMPRISING SOLUBLE CD84 OR ANTI-CD84 ANTIBODIES AND METHODS FOR DIAGNOSING AND TREATING B-CLL

(71) Applicant: Yeda Research and Development Co. Ltd., Rehovot, IL (US)

(72) Inventors: Idit Shachar, Ramat-Gan (IL); Inbal Binsky, Rehovot (IL); Mirko Sobotta, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 0 days.

(21) Appl. No.: 14/172,926

(22) Filed: Feb. 5, 2014

(65) Prior Publication Data

US 2014/0147451 A1 May 29, 2014

Related U.S. Application Data

(62) Division of application No. 13/120,442, filed as application No. PCT/IL2009/000919 on Sep. 23, 2009, now Pat. No. 8,686,121.

(60) Provisional application No. 61/136,651, filed on Sep. 23, 2008.

(51) Int. Cl.

| A61K 39/395 | (2006.01) |
| C07K 16/00 | (2006.01) |
| C07K 16/28 | (2006.01) |
| C07K 14/705 | (2006.01) |
| G01N 33/574 | (2006.01) |
| C12Q 1/68 | (2006.01) |
| A61K 38/00 | (2006.01) |

(52) U.S. Cl.  
CPC ........ *C07K 16/2803* (2013.01); *C07K 14/70596* (2013.01); *C12Q 1/6886* (2013.01); *G01N 33/57426* (2013.01); *A61K 38/00* (2013.01)

(58) Field of Classification Search  
CPC .............................. A61K 39/395; C07K 16/00  
USPC .............. 424/130.1, 141.1, 174.1; 530/388.1, 530/387.1  
See application file for complete search history.

(56) References Cited

U.S. PATENT DOCUMENTS

| 2003/0049618 A1* | 3/2003 | Ruben et al. ............... 435/6 |
| 2005/0025789 A1 | 2/2005 | Nieland et al. |
| 2005/0027114 A1 | 2/2005 | Kuo et al. |

FOREIGN PATENT DOCUMENTS

WO WO 2010/035259 4/2010

OTHER PUBLICATIONS

NCBI MeSH B-cell chronic lymphocytic leukemia.*  
Communication Relating to the Results of the Partial International Search Dated Feb. 2, 2010 From the International Searching Authority Re.: Application No. PCT/IL2009/000919.  
International Preliminary Report on Patentability Dated Apr. 7, 2011 From the International Bureau of WIPO Re. Application No. PCT/IL2009/000919.  
Bando et al. "Expression of Macrophage Migration Inhibitory Factor in Human Breast Cancer: Association With Nodal Spread", Japanese Journal of Cancer Research, 93: 389-396, Apr. 2002.  
Becker-Herman et al. "CD74 is a Member of the Regulated Intramembrane Proteolysis-Processed Protein Family", Molecular Biology of the Cell, 16: 5061-5069, Nov. 2005.  
Binsky et al. "IL-8 Secreted in a Macrophage Migration-Inhibitory Factor- and CD74-Dependent Manner Regulates B Cell Chronic Lymphocytic Leukemia Survival", Proc. Natl. Acad. Sci. USA, PNAS, 104(33): 13408-13413, Aug. 14, 2007.  
Brown et al. "2B4, the Natural Killer and T Cell Immunoglobulin Superfamily Surface Protein, is a Ligand for CD48", Journal of Experimental Medicine, XP002574396, 188(11): 2083-2090, Dec. 7, 1998. p. 2084, Col. 1, § 2, Fig.3, p. 2086, 2088.  
Calpe et al. "The SLAM and SAP Gene Families Control Innate and Adaptive Immune Responses", Advances in Immunology, 97(Chap. 4): 177-250, 2008.  
De La Fuente et al. "CD84 Leukocyte Antigen is a New Member of the Ig Superfamily", Blood, 90: 2398-2405, 1997.  
Matza et al. "Invariant Chain Induces B Cell Maturation by Activating a TAF[II]105-NF-KB-Dependent Transcription Program", The Journal of Biological Chemistry, 276(29): 27203-27206, Jul. 20, 2001.  
Matza et al. "Invariant Chain Induces B Cell Maturation in a Process That is Independent of Its Chaperonic Activity", Proc. Natl. Acad. Sci. USA, PNAS, 99(5): 3018-3023, Mar. 5, 2002.  
Matza et al. "Invariant Chain, A Chain of Command", Trends in Immunology, 24(5): 264-268, May 2003.  
Matza et al. "Invariant Chain-Induced B Cell Differentiation Requires Intramembrane Proteolytic Release of the Cytosolic Domain", Immunity, 17: 549-560, Nov. 2002.  
Mizue et al. "Quantitation of Macrophage Migration Inhibitory Factor (MIF) Using the One-Step Sandwich Enzyme Immunosorbent Assay: Elevated Serum MIF Concentrations in Patients With Autoimmune Diseases and identification of MIF in Erythrocytes", International Journal of Molecular Medicine, 5(4): 397-403, 2000.  
Narni et al. "HLA-DR-Associated Invariant Chain is Highly Expressed in Chronic Lymphocytic Leukemia", Blood, 68: 372-377, 1986.  
Nishihira et al. "Macrophage Migration Inhibitory Factor (MIF). Its Potential Role in Tumor Growth and Tumor-Associated Angiogenesis", Annals of the New York Academy of Sciences, 995: 171-182, 2003.

(Continued)

*Primary Examiner* — Yan Xiao

(57) ABSTRACT

A method of diagnosing B-CLL in a subject in need thereof is provided. The method comprising determining in a biological sample of the subject a level of CD84 isoform C (SEQ ID NO: 30), wherein an increase in the level of the CD84 isoform C (SEQ ID NO: 30) beyond a predetermined threshold with respect to a level of the CD84 in a biological sample from a healthy individual is indicative of the B-CLL.

6 Claims, 19 Drawing Sheets  
(3 of 19 Drawing Sheet(s) Filed in Color)

(56) References Cited

OTHER PUBLICATIONS

Palou et al. "Genomic Characterization of CD84 Reveals the Existence of Five Isoforms Differing in Their Cytoplasmic Domains", Tissue Antigens, 55: 118-127, 2000.
Shachar et al. "Requirement for Invariant Chain in B Cell Maturation and Function", Science, 274(5284): 106-108, Oct. 4, 1996.
Yan et al. "Structure of CD84 Provides Inaight Into SLAM Family Function", Proc. Natl. Acad. Sci. USA, XP002563816, 104(25): 10583-10588, Jun. 19, 2007. p. 10588.
Office Action Dated Jun. 29, 2014 From the Israel Patent Office Re. Application No. 228595 and Its Translation Into English.

\* cited by examiner

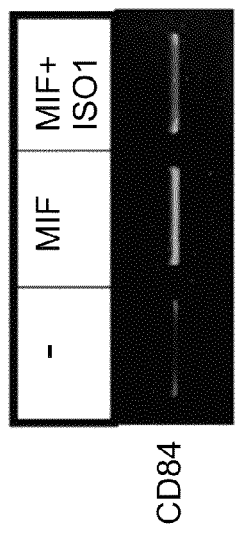
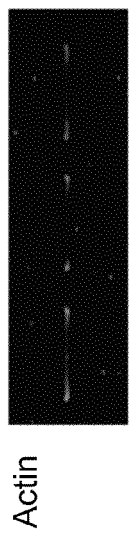
FIG. 2C
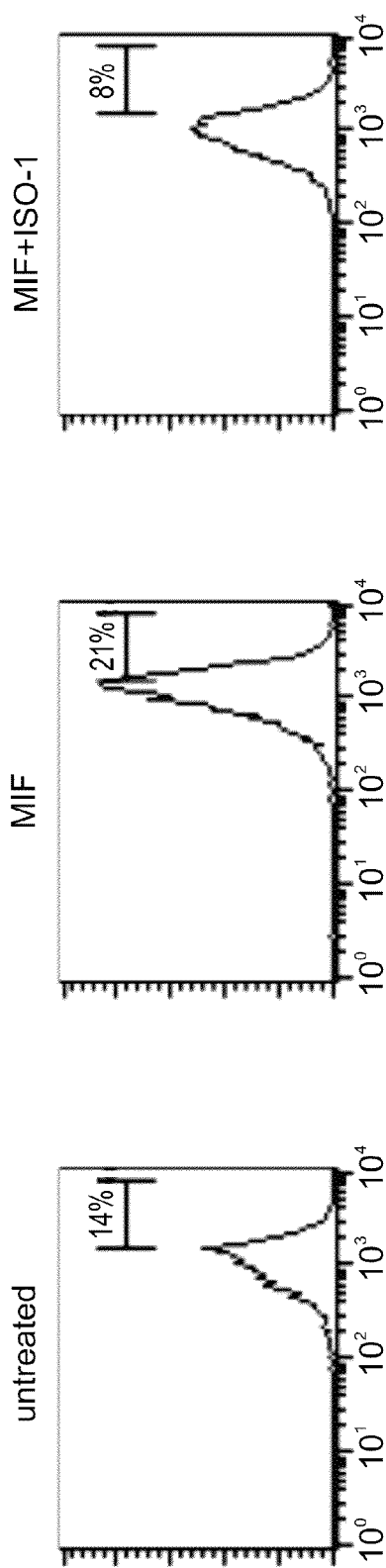
FIG. 2D

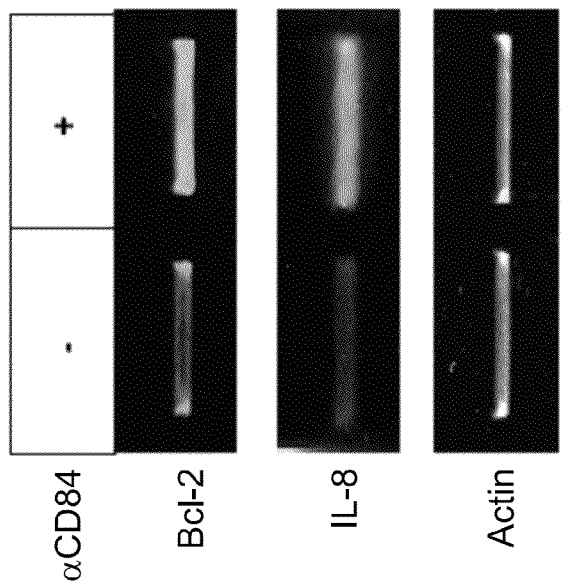
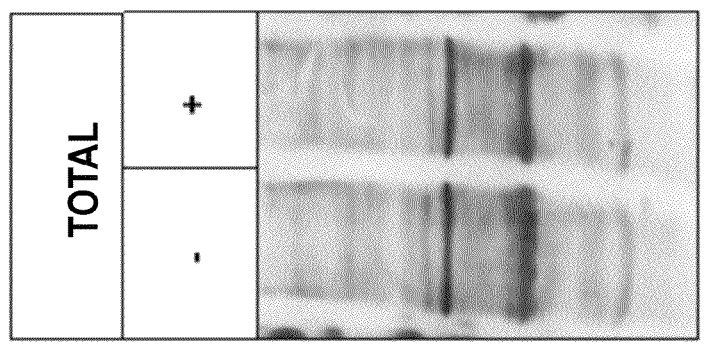
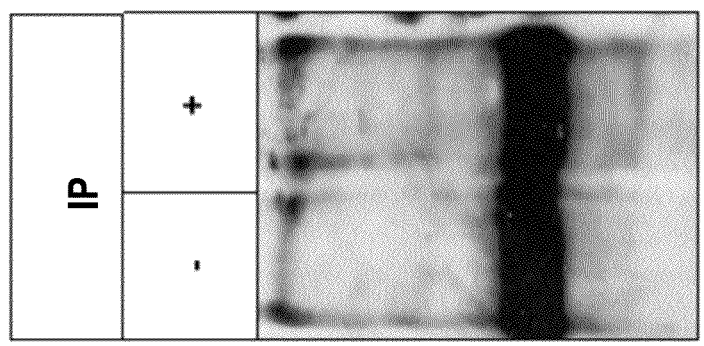
FIG. 3B
FIG. 3A

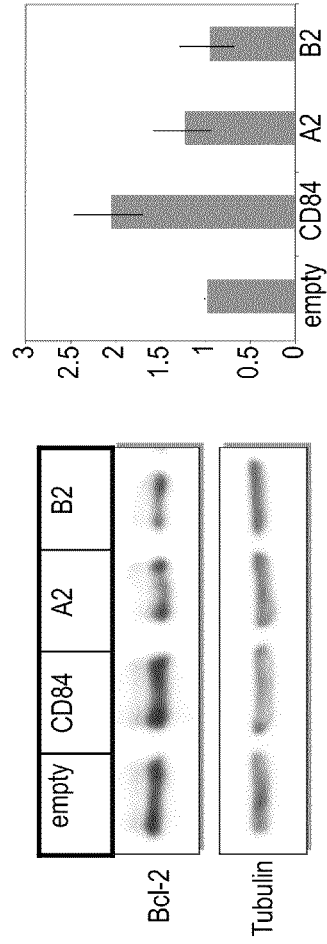
FIG. 8B
FIG. 8A
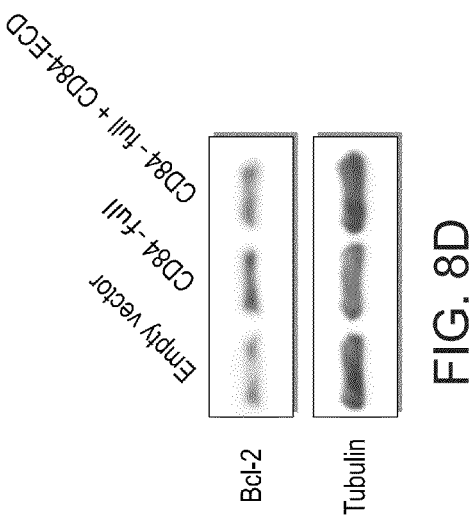
FIG. 8D
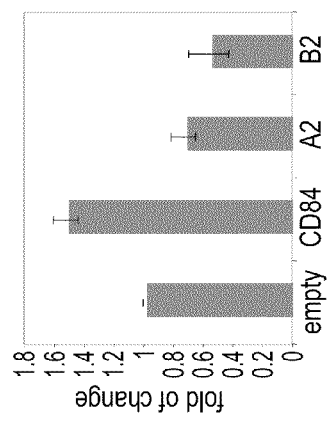
FIG. 8C

Protein analysis of purified CD84-ECD

Schematic view of CD84-ECD

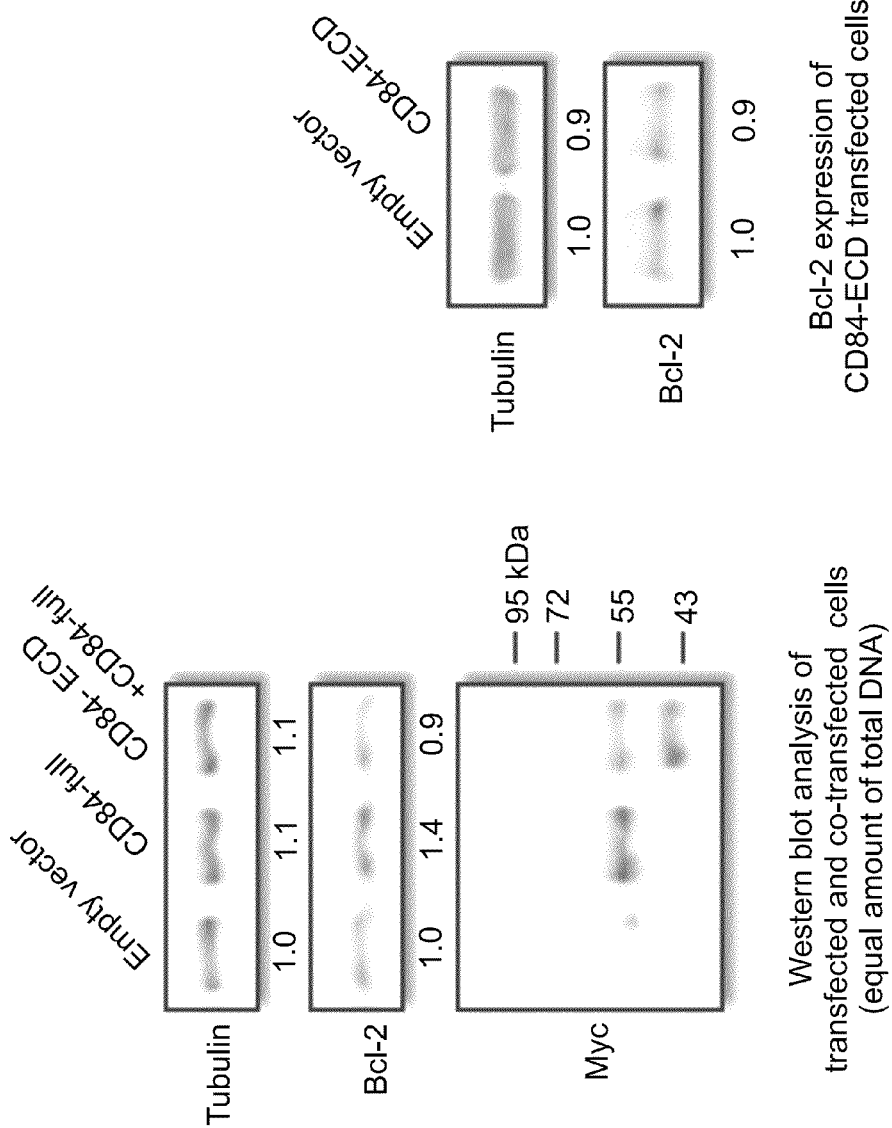

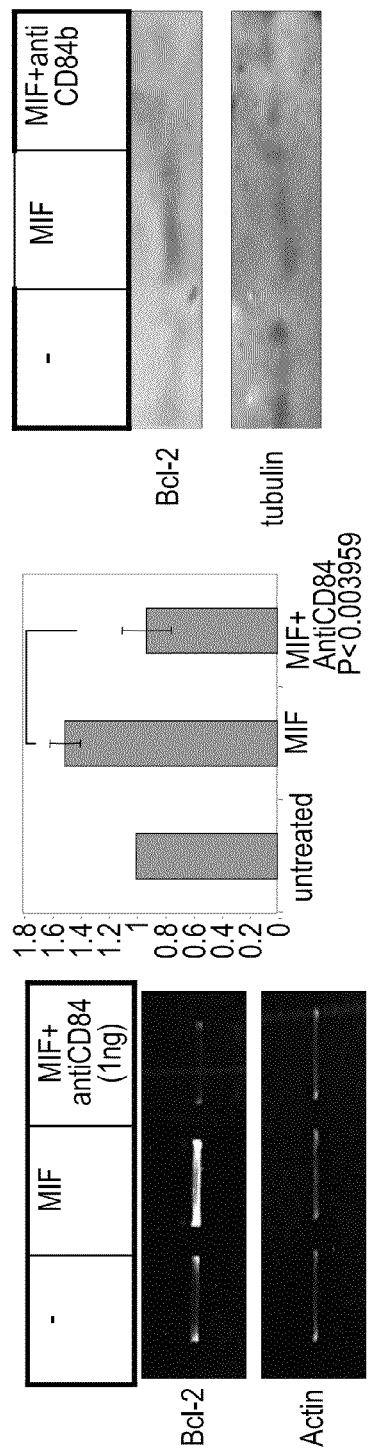

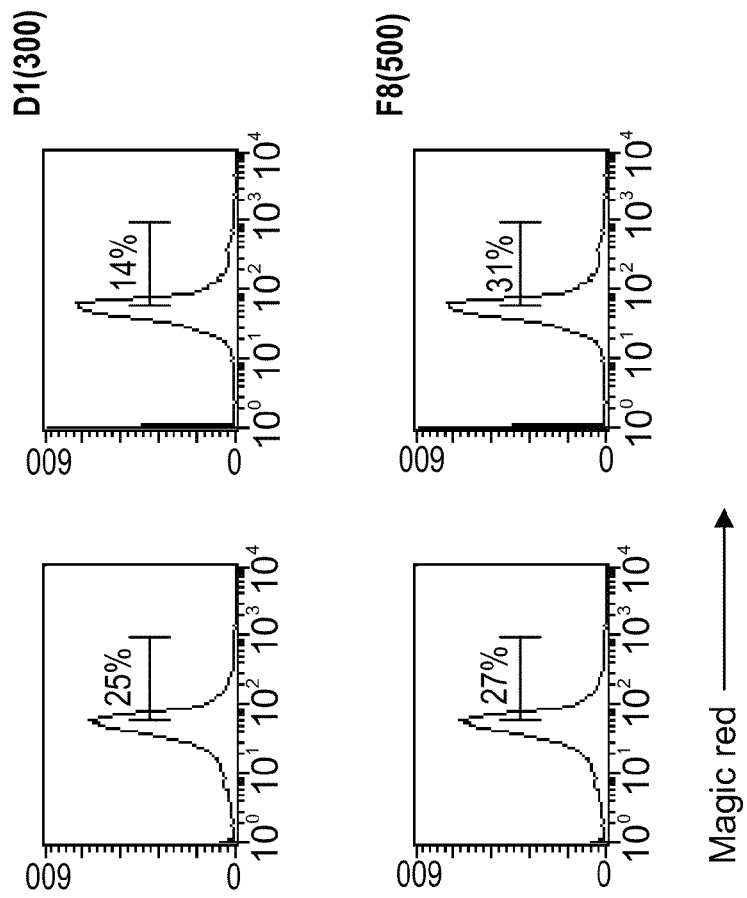
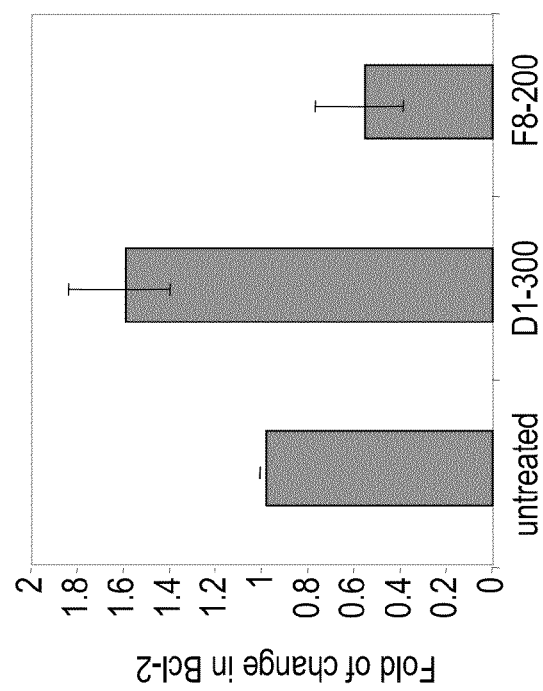
FIG. 16B
FIG. 16A

COMPOSITIONS COMPRISING SOLUBLE CD84 OR ANTI-CD84 ANTIBODIES AND METHODS FOR DIAGNOSING AND TREATING B-CLL

RELATED APPLICATIONS

This application is a division of U.S. patent application Ser. No. 13/120,442 (now U.S. Pat. No. 8,686,121) filed on Mar. 23, 2011, which is a National Phase of PCT Patent Application No. PCT/IL2009/000919 having International filing date of Sep. 23, 2009, which claims the benefit of priority of U.S. Provisional Patent Application No. 61/136,651 filed on Sep. 23, 2008. The contents of the above applications are all incorporated herein by reference.

SEQUENCE LISTING STATEMENT

The ASCII file, entitled 58320SequenceListing.txt, created on Feb. 4, 2014, comprising 96,768 bytes, submitted concurrently with the filing of this application is incorporated herein by reference.

FIELD AND BACKGROUND OF THE INVENTION

The present invention, in some embodiments thereof, relates to compositions and methods for diagnosing and treating B-CLL.

In normal individuals, the pool of peripheral lymphocytes is constant in size. The control of lymphoid homeostasis is the result of a very fine balance between lymphocyte production, survival, and proliferation. Survival factors have been shown to play a critical role in maintaining lymphocyte homeostasis.

Chronic lymphocytic leukemia, the most common leukemia in the Western world, is characterized by the progressive accumulation of CD5$^+$ small mature lymphocytes, in the peripheral blood, lymphoid organs and bone marrow. The hallmark of the disease is decreased apoptosis, resulting in accumulation of these malignant cells. Despite major progress in the last few years in the understanding of the biology and pathophysiology of the disease, as well as the development of better treatment modalities, CLL remains incurable in most patients, and even control of the disease requires aggressive treatment with significant side effects. A better understanding of the cellular events involved in the pathogenesis and progression of the disease should lead to more targeted and less toxic therapies, with early treatment in patients at risk, possibly enabling cure.

Previous studies have shown that CLL lymphocytes express relatively large amounts of the CD74 (invariant chain; Ii) mRNA compared to normal B cells, and this receptor regulates cell survival in an IL-8 dependent manner.

CD74 is a non-polymorphic type II integral membrane protein that is expressed on antigen presenting cells, including macrophages and B cells. It has a short N-terminal cytoplasmic tail of 28 amino acids (aa), followed by a single 24 aa transmembrane region, and a lumenal domain of approximately 150 aa. The CD74 chain was initially thought to function mainly as an MHC class II chaperone, which promotes ER exit of MHC class II molecules, directs them to endocytic compartments, prevents peptide binding within the ER, and contributes to peptide editing in the MHC class II compartment. A small proportion of CD74 is modified by the addition of chondroitin sulfate (CD74-CS), and this form of CD74 is expressed on the surface of antigen presenting cells. It was previously shown that macrophage migration inhibitory factor (MIF) binds to the CD74 extracellular domain on macrophages, a process that results in the initiation of a signaling pathway in these cells. MIF promotes monocyte/macrophage activation and is required for the optimal expression of TNF, IL-1 and PGE$_2$. MIF-activated macrophages are more phagocytic and better able to destroy intracellular pathogens, such as *Leishmania*.

CD44 is a broadly-expressed single-pass transmembrane protein with known kinase-activating properties.

Recently, CD44 was described as an integral component of the CD74 receptor complex. While CD74 is sufficient for the binding of MIF to the cell surface, CD44 was found to be necessary for MIF signal transduction. CD74 expressed on B cells is directly involved in shaping the B cell repertoire by regulating mature B cell survival [Shachar et al. Science. 1996; 274:106-108; Matza et al. Proc Natl Acad Sci USA. 2002; 99:3018-3023; Matza et al. 2003 Trends Immunol. 24:246-248] through a pathway leading to the activation of transcription mediated by the NF-κB p65/RelA homodimer and its co-activator, TAFII105 [Matza et al. J Biol Chem. 2001; 276:27203-27206]. NF-κB activation is mediated by the cytosolic region of CD74 (CD74-ICD), which is liberated from the membrane [Matza et al. Immunity. 2002; 17:549-560]. Following the removal of the CD74 lumenal domain, an intramembranal cleavage event occurs at amino acid 42, resulting in the release of the CD74 cytosolic fragment (CD74-ICD; aa 1-42). CD74-ICD then translocates to the cell nucleus and activates NF-κB [Becker-Herman Cell. 2005; 16:5061-5069]. Thus, following this processing step, CD74 acts as a signaling molecule that induces accumulation of mature B cells. This signal is attenuated by degradation of the active CD74-ICD fragment, and its removal from the cytoplasm. Moreover, CD74 stimulation by MIF leads to NF-κB activation, enabling entry of the stimulated B cells into the S phase, an increase in DNA synthesis, cell division, and augmented expression of anti-apoptotic proteins in a CD44 dependent manner. These findings indicate that surface CD74 functions as a survival receptor.

Interestingly, both MIF and CD74 have been associated with tumor progression. It was reported that MIF mRNA is over-expressed in various tumors and MIF has also been associated with the growth of malignant cells [Bando et al. Jpn J Cancer Res. 2002; 93:389-396; Nishihira et al. Ann NY Acad Sci. 2003; 995:171-182]. Many studies have demonstrated the overexpression of CD74 in various cancers including CLL [Narni et al. Blood. 1986; 68:372-377]. CD74 expression in many of these cancers has been suggested to serve as a prognostic factor, with higher relative expression of CD74 behaving as a marker of tumor progression [Mizue et al. Int J Mol Med. 2000; 5:397-403]. Activation of CD74 by MIF on B-CLL cells, initiates a signaling cascade that contributes to tumor progression. This pathway induces NF-κB activation, resulting in the secretion of interleukin 8 (IL-8), which in turn promotes cell survival. Blocking of this pathway leads to decreased cell survival. Thus, CD74 expressed on the surface of B-CLL cells plays a critical role in regulating the survival of these malignant cells [Binsky et al. Proc Natl Acad Sci USA. 2007; 104:13408-13413]. Molecules which participate in CD74 signaling may thus be used as new targets and generation of therapeutic platforms for the treatment of chronic lymphoid leukemia.

CD84 is a member of the CD2 subset of the immunoglobulin superfamily of cell surface molecules. It is a single chain cell-surface protein with an extracellular portion of 199 aa, which contains four potential N-glycosylation sites. The transmembrane region consists of 25 aa, and the 83 aa cytoplasmic tail contains four tyrosines [delaFuente et al. Blood.

1997; 90:2398-2405]. The human CD84 is 57.3% identical to murine CD84. CD84 is predominantly expressed by B cells, T cells, platelets, monocytes, dendritic cells (DCs), and CD84 is also expressed early in hematopoiesis [Calpe et al. Advances in Immunology, Vol 97. 2008; 97:177-250].

Based on the expression of CD84, B cells can be subdivided into $CD84^{hi}$ and $CD84^{lo}$ populations. The $CD84^{hi}$ population represents a subset of memory B cells, which are characterized by co-expression of CD27, somatically mutated Ig variable region genes, and vigorous proliferation in response to CD40L and IL-4, compared to $CD84^{lo}$ B cells.

Nevertheless, the role of CD84 in the biology of these cells is not known. A striking feature of human CD84 is the expression of a complex series of isoforms with several cytoplasmic tails in tumor cells [Palou et al. Tissue Antigens. 2000; 55:118-127]. The expression and functional relevance of these variants are still unknown. Two CD84 transcripts have been described to date in murine tissues. CD84 strongly self-associates with a Kd in the submicromolar range; the association is driven by the Ig-V domain, forming an orthogonal homophilic dimer.

Additional Related Art:

U.S. Patent Application Number 20050027114 discloses methods of treating diseases such as chronic leukemia by agonizing or antagonizing an activity of a cd84-like polypeptide.

U.S. Patent Application Number 20050025789 discloses the treatment or prophylaxis of tumors in patients, using a costimulatory polypeptide (e.g., CD84)-expressing tumor cell for producing a vaccine for increasing the lytic activity of NK cells.

SUMMARY OF THE INVENTION

According to an aspect of some embodiments of the present invention there is provided a method of diagnosing B-CLL in a subject in need thereof, the method comprising determining in a biological sample of the subject a level of CD84 isoform C (SEQ ID NO: 30) wherein an increase in the level of the CD84 isoform C (SEQ ID NO: 30) beyond a predetermined threshold with respect to a level of the CD84 in a biological sample from a healthy individual is indicative of the B-CLL.

According to an aspect of some embodiments of the present invention there is provided a use of an agent which decreases activity or expression of CD84 in the manufacture of a medicament for treating B-CLL.

According to an aspect of some embodiments of the present invention there is provided a use of an agent which decreases activity or expression of CD84 for treating B-CLL.

According to an aspect of some embodiments of the present invention there is provided a method of inducing apoptosis in a B cells of a subject having B-CLL, the method comprising administering to the subject a therapeutically effective amount of an agent which decreases activity or expression of CD84, thereby inducing apoptosis in B cells of the subject.

A method of treating B-CLL in a subject in need thereof, the method comprising administering to the subject a therapeutically effective amount of an agent which decreases activity or expression of CD84, thereby treating B-CLL.

According to an aspect of some embodiments of the present invention there is provided an isolated polypeptide comprising an amino acid sequence of a soluble CD84, wherein the soluble CD84 binds CD84 expressed on B cells and inhibits its homophilic interaction.

According to an aspect of some embodiments of the present invention there is provided a pharmaceutical composition comprising a soluble CD84, wherein the soluble CD84 binds CD84 expressed on B cells and inhibits its homophilic interaction.

According to an aspect of some embodiments of the present invention there is provided an isolated polypeptide having the CDR sequences of the anti CD84 extracellular domain antibody produced by the hybridoma which has been deposited at the CNCM Pasteur Institut under the deposit number CNCM I-4228 (F8). The name and address of the depositor is CNCM—Collection Nationale de Cultures de Microorganismes, Institut Pasteur, 25 Rue du Docteur Roax, F-75724 Paris Cedex 15, France. According to some embodiments of the invention, the polypeptide is an antibody or an antibody fragment.

According to some embodiments of the invention, the biological sample comprises B cells and wherein the determining is in the B cells.

According to some embodiments of the invention, the determining is effected at the mRNA level.

According to some embodiments of the invention, the determining is effected at the protein level.

According to some embodiments of the invention, the method further comprising corroborating the diagnosis using a diagnostic assay selected from surface marker expression distinctive of the CD84 isoform c, karyotype analysis and germline mutations.

According to some embodiments of the invention, the method further comprising informing the subject of the disease.

According to some embodiments of the invention, the agent comprises a soluble CD84, wherein the soluble CD84 binds CD84 expressed on B cells and inhibits its homophilic interaction According to some embodiments of the invention, the soluble CD84 comprises an extracellular domain of CD84 and is devoid of a transmembrane domain of CD84.

According to some embodiments of the invention, the soluble CD84 is fused to a moiety for increasing solubility of the soluble CD84.

According to some embodiments of the invention, the soluble CD84 is as set forth in SEQ ID NO: 2.

According to some embodiments of the invention, the agent comprises a nucleic acid agent which decreases expression of the CD84.

According to some embodiments of the invention, the agent comprises a CD84 neutralizing antibody.

According to some embodiments of the invention, an isolated polynucleotide comprising the nucleic acid sequence encoding the soluble CD84.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
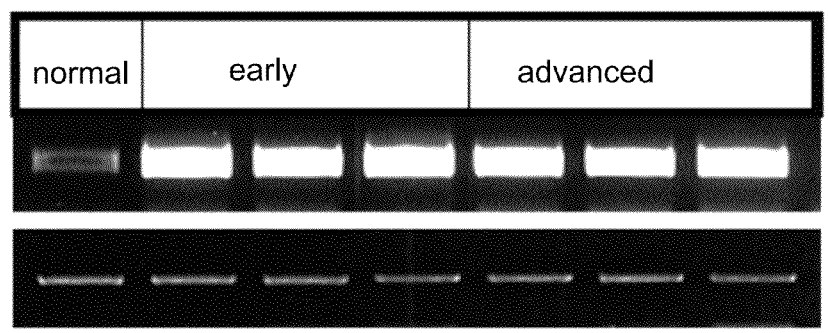
Figure 1B:
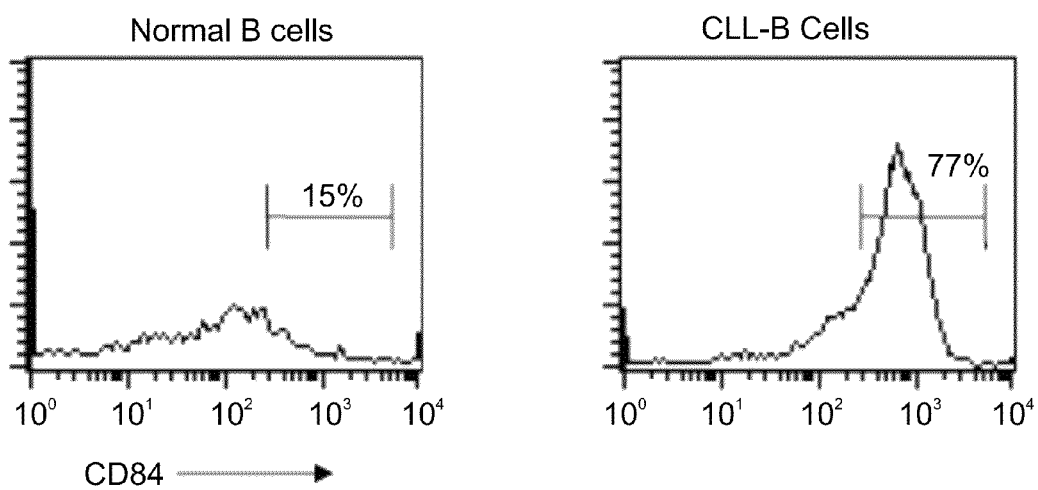

FIGS. 1A-B show elevated expression of hCD84 in B-CLL cells. B cells derived from healthy subjects (normal), as well as early- and advanced-stage B-CLL patients, were purified. (A) CD84 mRNA was analyzed by RT-PCR. The results presented are representative of 2 normal, 6 early-stage, and 6 advanced-stage B-CLL patients. (B) Cells were stained with anti-CD84. Histograms show CD84 expression on B-CLL as well as on normal B cells. The results presented are representative of 2 normal, 7 early-stage, and 6 advanced-stage B-CLL patients.

FIGS. 2A-D show that CD84 is a target gene of CD74 in B-CLL cells. (A, B) B cells derived from B-CLL patients were purified. Cells were incubated in the presence or absence of MIF. (A) Following 18 h, RNA was purified, and CD84 and actin mRNA was analyzed. The results presented are representative of 6 early and 4 advanced B-CLL patients. (B) Following 24 h, cells were stained with anti-CD84. Histograms show CD84 expression on B-CLL. The results presented are representative of 3 early and 6 advanced B-CLL patients. (C, D) B-CLL cells were incubated in the presence or absence of MIF (100 ng/ml), ISO-1 (20 mM). (C) Following 18 h, RNA was purified and levels of CD84 and actin mRNA were analyzed. The results presented are representative of 4 B-CLL patients. (D) Following 24 h, cells were stained with anti-CD84. Histograms show CD84 expression on B-CLL. The results presented are representative of 5 B-CLL patients.

FIGS. 3A-B show that activation of cell surface CD84 initiates tyrosine phosphorylation and a survival cascade in B-CLL cells. B-CLL cells were incubated in the presence or absence of anti-CD84 (1 ng/ml) for 30 minutes. The cells were then washed, and bound mAb was cross-linked with F(ab')2 gout anti mouse Ig. (A) Cells were immunoprecipitated with anti-pTyr over night and lysed. Lysates were separated on 8% (wt/vol) SDS/PAGE and blotted with anti-CD84 antibody (results presented are representative of 3 separate experiments). (B) Following 18 h, RNA was purified and levels of Bcl-2, IL-8 and actin mRNA were analyzed. The results presented are representative of 7 B-CLL patients.

Figures 4A, 4B:
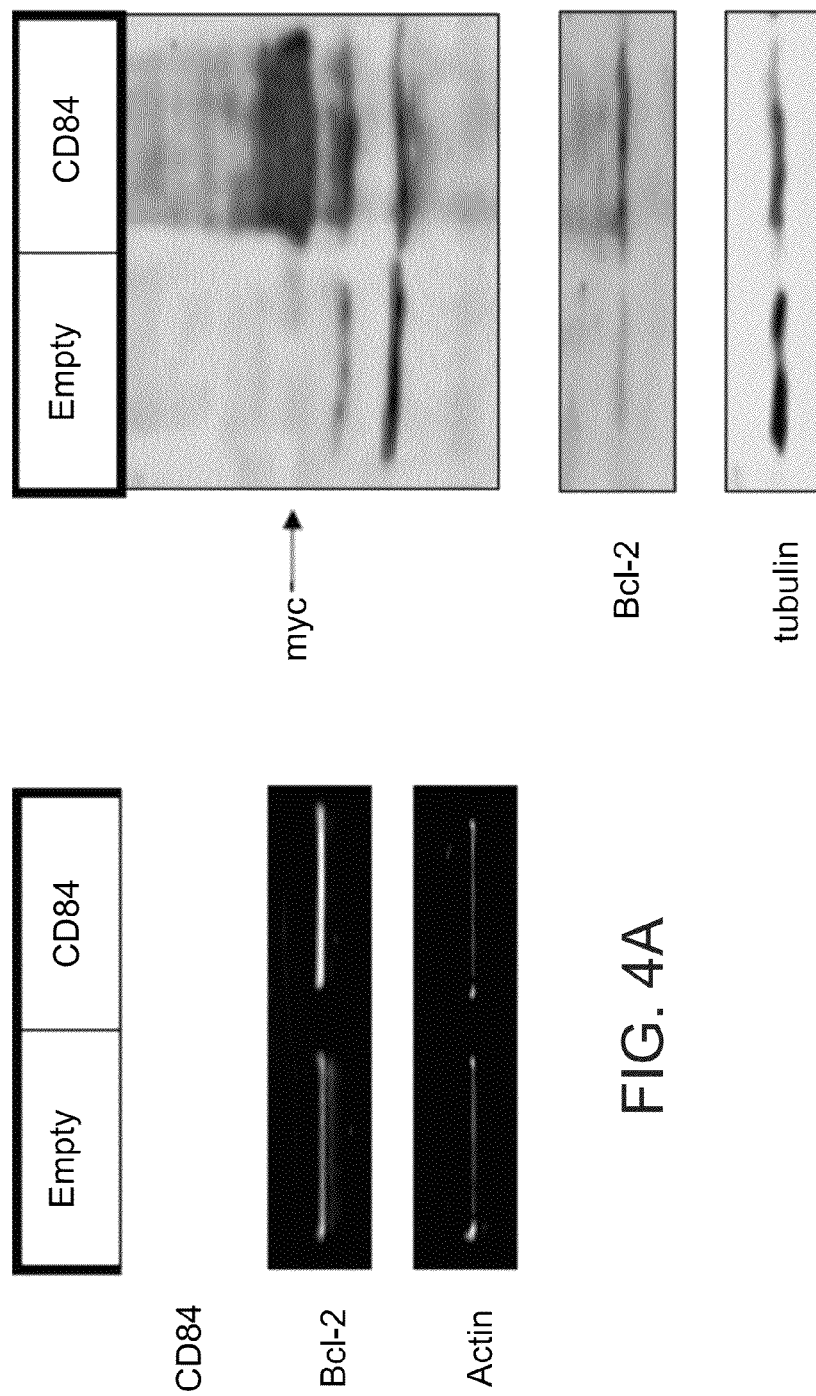

FIGS. 4A-B show that activation of cell surface CD84 initiates a survival cascade in HEK 293 cells. HEK-293 cells transfected with full-length (FL) CD84 or with an empty plasmid constructs. (A) Following 8 h, RNA was purified and levels of CD84, Bcl-2, and actin mRNA were analyzed. The results presented are representative of 2 independent experiments with similar results. (B) Following 24 hours, cells were lysed by hot SDS, and the lysates were then separated on 12% (wt/vol) SDS/PAGE and blotted with anti-Myc, anti-Bcl-2 and tubulin antibody, followed by anti-mouse HRP antibodies. The results shown represent 8 independent experiments with similar results.

Figure 5:
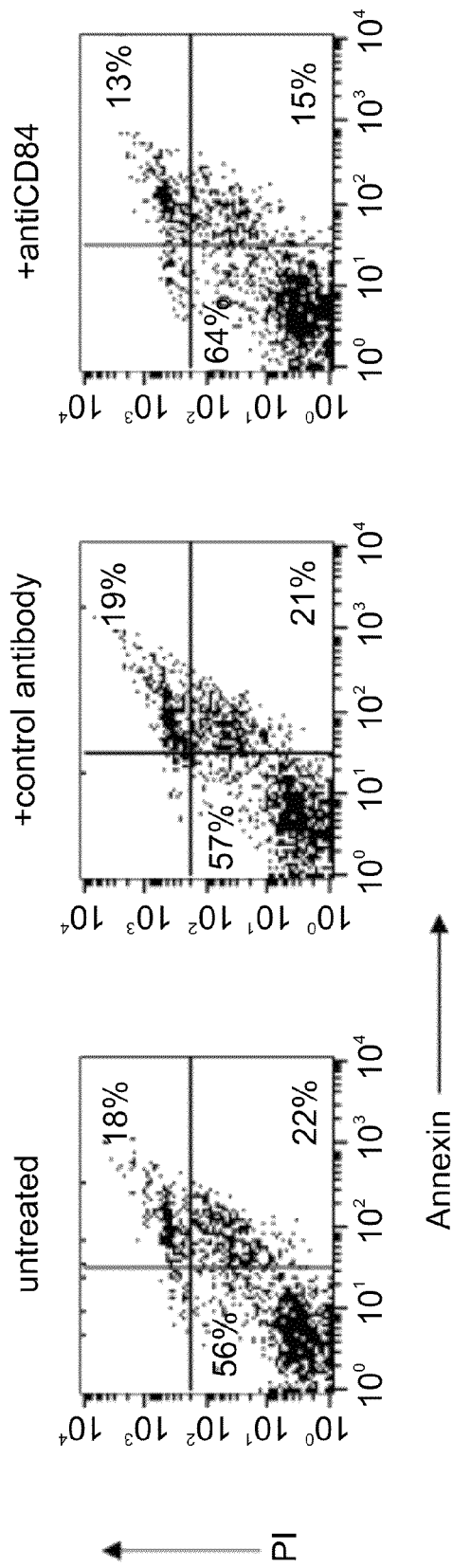

FIG. 5 shows that activation of cell surface CD84 induces a survival cascade in B-CLL cells. B-CLL cells were incubated in the presence or absence of anti-CD84 (1 ng/ml) for 30 minutes. The cells were then washed, and bound mAb was cross-linked with F(ab')2 gout anti mouse Ig for 26 h. Cells were stained with annexin V, PI and analyzed by FACS. The results presented are representative of 7 B-CLL patients.

Figures 6A, 6B:
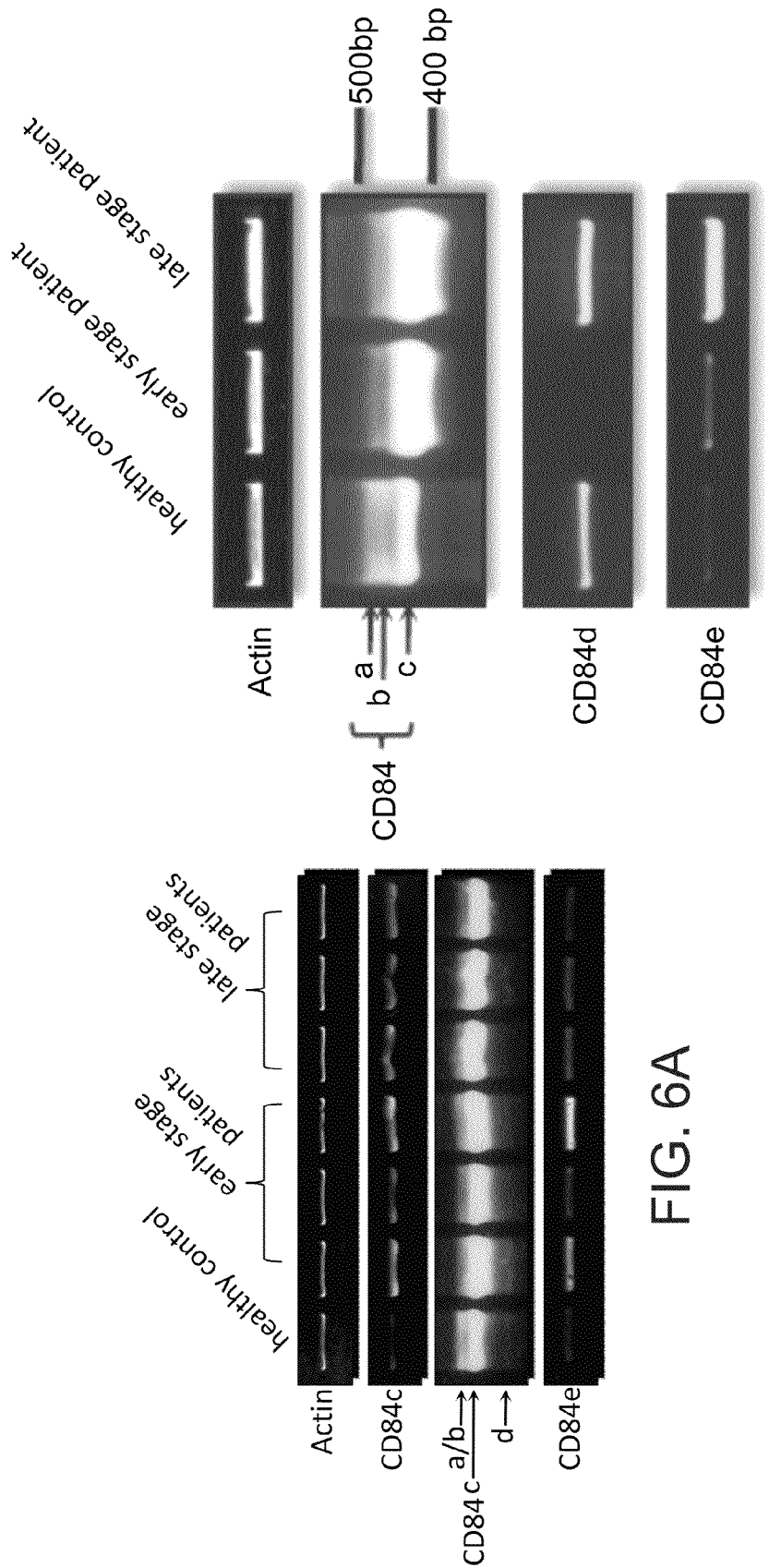

FIGS. 6A-B show analyses of mRNA coding CD84 isoforms. Total RNA, isolated from human B lymphocytes (either healthy control person, stage I or stage IV B-CLL patients) was subjected to semi-quantitative RT-PCR with actin as a reference gene and analysed by 3% agarose gel electrophoresis. The shown results are exemplary for the overexpression of CD84C in B-CLL patients. The corresponding PCR product sizes for the different isoforms are: a—477 bp; b—459 bp; c—426 bp; d—500 bp; e—272 bp. The arrows on the left indicate the identity of the RT-PCR products.

Figure 7:
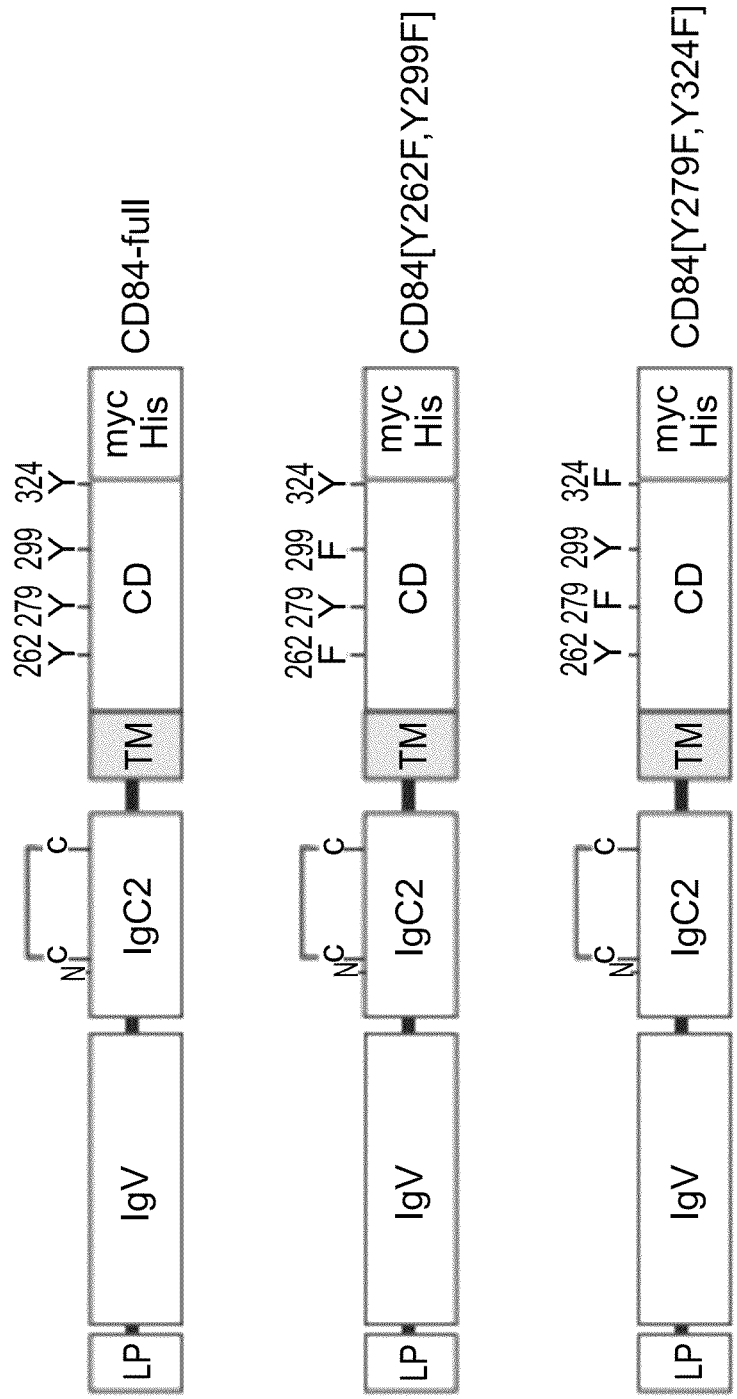

FIG. 7 is a schematic illustration of the CD84—full construct and tyrosine mutated versions. Lp—leader peptide; IgV—immunoglobulin domain type V; immunoglobulin type C2; TM—transmembrane; CD—cytoplasmic domain; myc/His—different tags. One letter amino acid designations are above diagrams "N" indicates predicted site of N-glycosylation, interconnected "C" indicate disulfide bonds. Length of construct 367 amino acids.

FIGS. 8A-D describe the double mutations CD84 (Y262/Y299 or Y279/Y324) and their effects on down regulation of Bcl-2 in CD84 transfected 293 cells: FIGS. 8A-C—293 cells were transfected with empty vector, CD84 full, CD84 (Y262F, Y299F)=A2 and CD84(Y279F, Y324F)=B2. FIG. 8A—18 h post transfection RNA was purified. Quantitative Real time PCR was performed using primers for Bcl-2 and RP-2. qRTPCR—Results are expressed as a fold of change in Bcl-2 expression compared to empty, which was defined as 1. N=3 transfections. FIG. 8B—40 h post transfection cells Lysates were subjected to analysis by 12% SDS-PAGE and Western blot. The graph shows the average fold change in Bcl-2 Expression of 6 different experiments. FIG. 8C—6 h after transfection the medium was replenished and CD84 was activated using CD84 activating antibody. 24 h later the cells were harvested and subjected to 12% SDS-PAGE and Western blot analysis for Bcl-2 expression. The graph shows the average fold change in Bcl-2 expression of 4 different experiments. FIG. 8D—293 cells were transfected with empty vector, CD84 full, or CD84 full plus CD84-ECD. The cells were subjected to 12% SDS-PAGE and Western blot analysis for Bcl-2 expression. The results Presented are representative out of 5.

Figure 9:
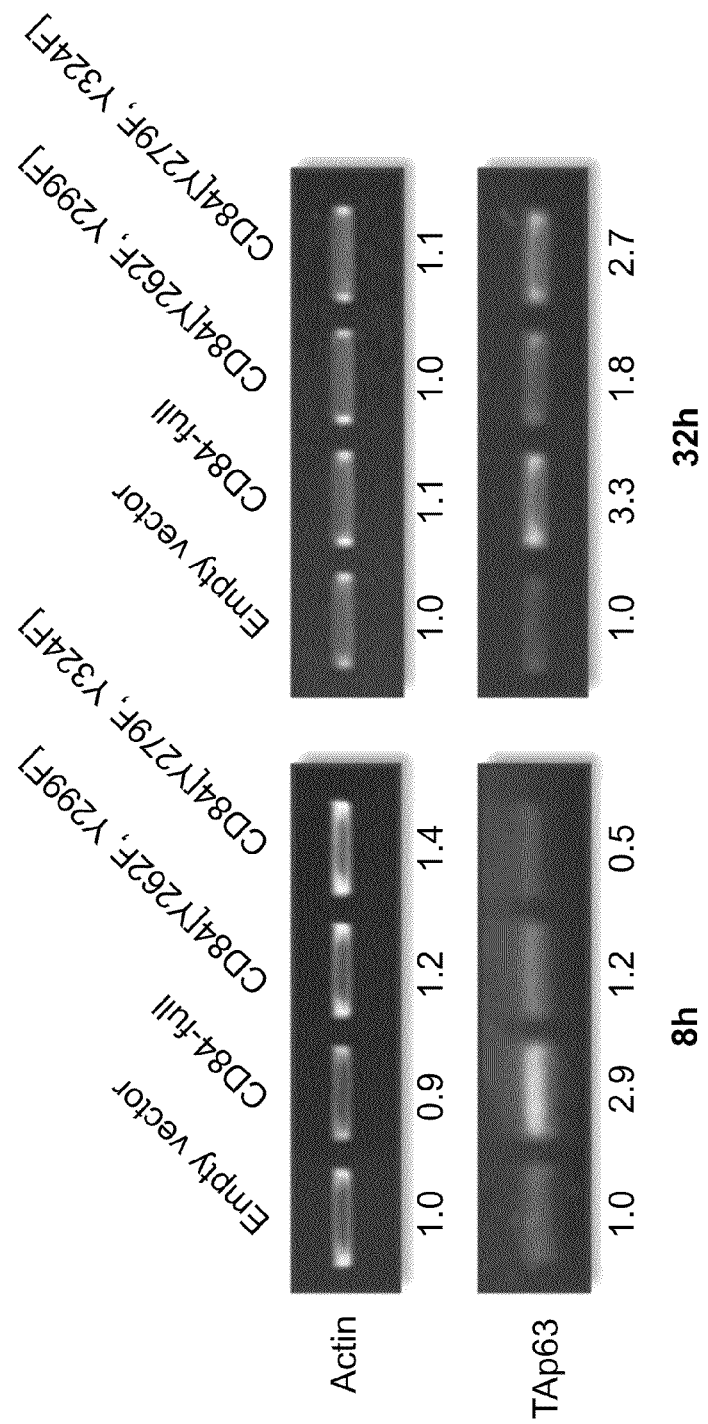

FIG. 9 show overexpression of un-mutated and tyrosine mutated CD84 affects the Tap63 expression. HEK 293T cells were transfected with pEF4 (empty vector), Cd84-full (un-mutated) and CD84 double mutants as indicated. 8 h or 32 h post transfection the cells were subjected to semiquantitative RT-PCR with actin as a reference gene, following analysis by 1.5% agarose gel electrophoresis. The results of two independent experiments are shown.

FIGS. 10A-D show the design, purification and identification of CD84-ECD. (extracellular domain). (A) The scheme is drawn true to scale. See abbreviations as in FIG. 7 above. Length of construct 330 amino acids. (B, C) Samples of different purification stages were analyzed on 12% SDS-PAGE and Western blot analysis with anti-Myc antibody (B) or Coomassie staining (C). Conditioned medium (lane 7) was purified with $Ni^{2+}$—metal chelate affinity chromatography (lane 1+5), followed by size exclusion chromatography. Lane 2-4 show the peak fractions of the size exclusion chromatography. (D) identification of CD84 construct by ESI-MS/MS. The excised gel fragment of the Coomassie stained gel (c, lane 3) was analysed with limited proteolysis followed by ESI-MS/MS. The protein sequence is set in SEQ ID NO: 26.

Matched peptides for Cd84 are highlighted in red. This analysis was performed by the Biological Service Unit of the Weizmann Institute.

Figure 11:
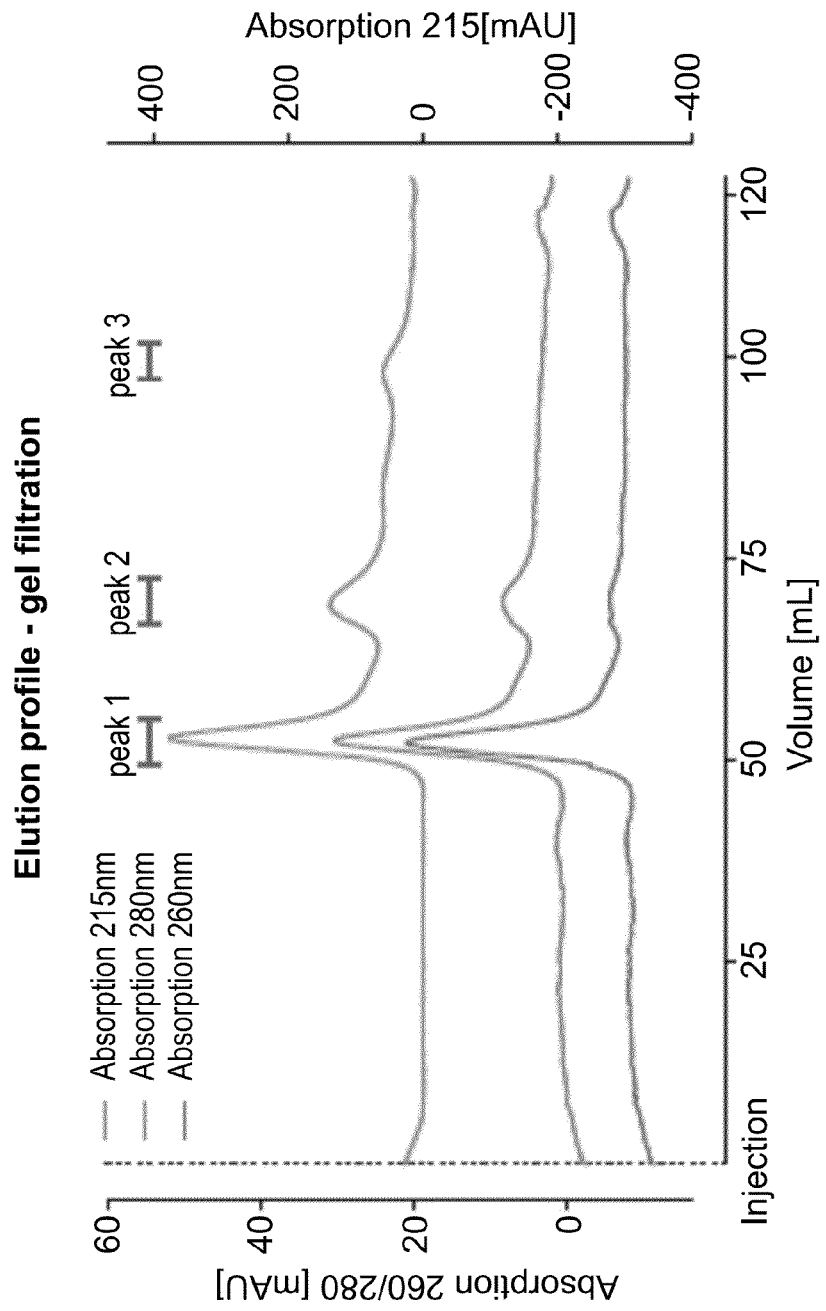

FIG. 11 is a graph of size exclusion chromatography-FPLC (SEC-FPLC) elution profile for CD84-ECD protein. The graph shows a typical elution profile at 215, 260 and 280 nm. The peaks corresponding to the analyzed fraction are indicated by bars labeled with peak 1-3. The separation was performed on GE Healthcare HiLoad 16/60 Superdex 200 column.

Figure 12C:
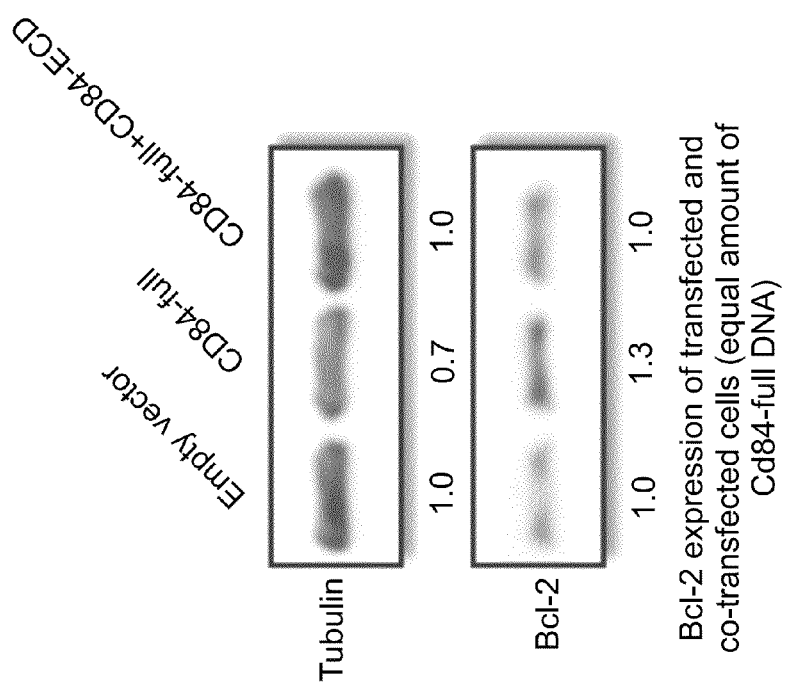

FIGS. 12A-C are photomicrographs showing the blocking effect of CD84-ECD on CD84-Bcl-2 induced activation. (A) HEK 293T cells were transfected with 2 µg pEF4 (empty vector), 2 µg CD84-full or 1 µg CD84-ECD to give a final amount of 2 µg DNA. The cells were subjected to 12% SDS-PAGE and Western blot as indicated. (B) HEK 293Y cells were transfected with equal amounts of pEF4 (empty vector) and CD84-ECD and subjected to 12% SDS-PAGE and Western blot as indicated. (C) Western blot analysis of transfected and co-transfected cells (equal amount of CD84-full DNA). HEK 293T cells were transfected with 2 µg pEF4 (empty vector), 2 µg CD84-full or 2 µg CD84-ECD plus 2 µg of CD84-ECD and subjected to 12% SDS-PAGE and western blot analysis as described above. The total amount of DNA was kept constant by adding empty pEF4 plasmid.

Figure 13:
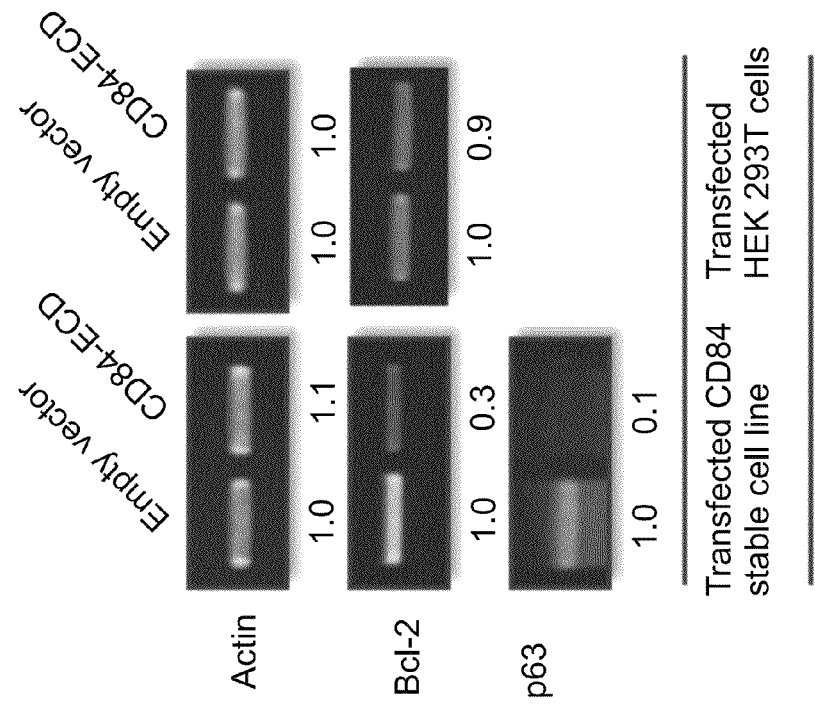

FIG. 13 show the effect of CD84 ECD on Bcl-2 expression. The CD84s20 cell line or HEK 293T cells were transfected with pEF4 (empty vector) or CD84-ECD. Twenty four hours following transfection, total RNA was isolated, subjected to RT-PCR for the indicated genes.

Figure 14:
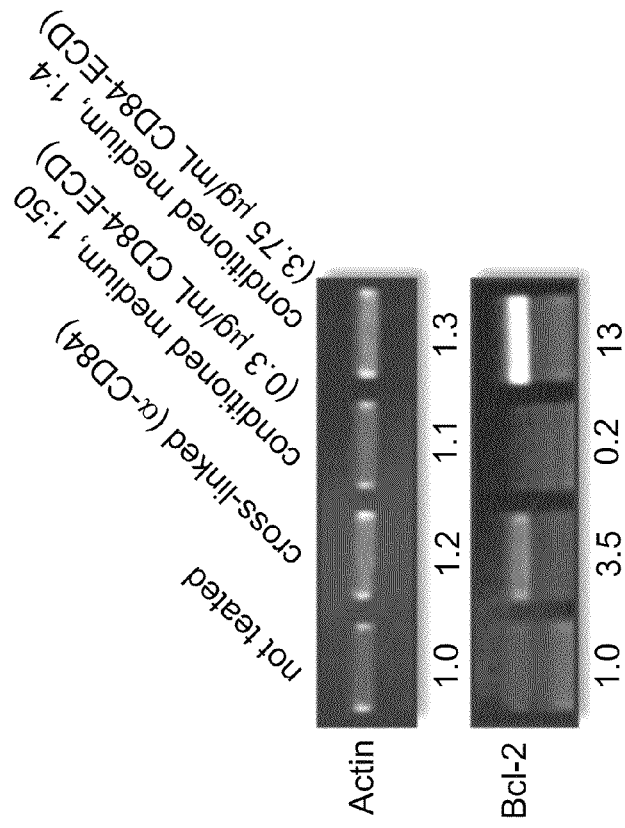

FIG. 14 show the effect of CD84 ECD conditioned medium on BCL-2 expression. Surface CD84 of the CD84s20 cell line was or was not cross-linked with anti-CD84 and anti-Fab antibody in the presence or absence of different concentrations of CD84-ECD. Twenty four hours following treatment, total RNA was isolated, and RT-PCR for Bcl-2 and actin was performed.

FIGS. 15A-C show that an anti CD84 blocking antibody induces B-CLL death. B-CLL cells were incubated in the presence or absence of MIF and CD84 blocking antibody. FIG. 15A—After 18 hours, RNA was purified. Bcl-2 and actin mRNA levels were analyzed. N=4 patients. Quantitative Real time PCR was performed using primers for Bcl-2 and RP-2. qRTPCR—Results are expressed as a fold of change in Bcl-2 expression by stimulated cells compared to non-stimulated cells, which was defined as 1. N=3 patients. FIG. 15B—Cells were lysed after 24 hr exposure to MIF and CD84 blocking antibody, and Bcl-2 and tubulin expression were analyzed by Western blot analysis. FIG. 15C—27 hours after application of MIF and cd84 blocking antibody, cells were stained with FLICA, and analyzed by FACS. N=5 patients.

FIGS. 16 A-B show the effect of Ab from hybridoma D1-300, F8-200 and F8-500 (different concentrations of the antibody) on B-CLL survival. FIG. 16A—B-CLL cells were incubated in the presence or absence of conditioned medium derived from hybridoma D1-300 or F8-200 for 18 h. RNA was purified. Quantitative Real time PCR was performed using primers for Bcl-2 and RP-2. qRTPCR—Results are expressed as a fold of change in Bcl-2 expression by stimulated cells compared to non-stimulated cells, which was defined as 1. N=3 patients. FIG. 16B—Cells were incubated in the presence or absence of sup hybridoma for 24 h, cells were stained with magic red, and analyzed by FACS. N=1 patients.

Figure 17:
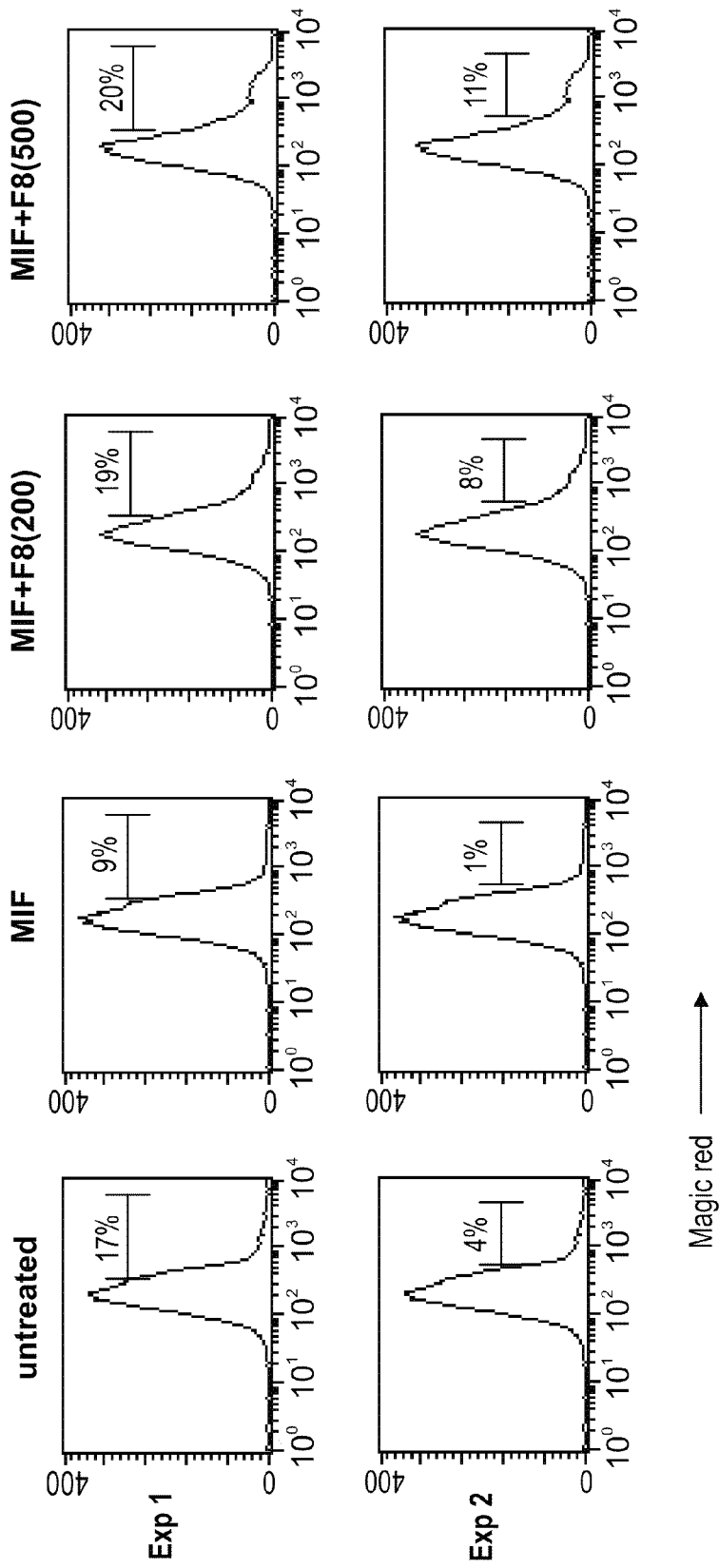

FIG. 17 shows the effect of antibodies from hybridoma F8-200 and F8-500 on B-CLL survival. Cells were incubated in the presence or absence of MIF and conditioned medium derived from hybridoma F8-200 or F8-500 for 24 h, cells were stained with magic red, and analyzed by FACS. N=1 patients.

DESCRIPTION OF EMBODIMENTS OF THE INVENTION

The present invention, in some embodiments thereof, relates to compositions and methods for diagnosing and treating B-CLL.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Chronic lymphocytic leukemia (CLL), a malignant disease characterized by the accumulation of B lymphocytes in the blood, lymphoid organs, and bone marrow, is the second most common type of leukemia in adults, accounting for about 7,000 new cases of leukemia each year. Presently, there is no cure for CLL, and the overall goal of leukemia treatment is to bring about a remission. Therefore, identifying new proteins that may serve as a target for inducing cell death in the malignant cells is highly desirable.

The present inventors have identified CD84 as a regulator protein that is essential for the survival of CLL cells. As is illustrated hereinbelow and in the Examples section which follows, the present inventors were able to show that B cells taken from CLL patients express a high level of CD84 isoform C as compared to expression of same in B cells of healthy subjects free of the disease. Stimulation of CD84 by MIF, upregulated the survival of B-CLL, as was evidenced by upregulation of Bcl-2 and reduction in annexin staining all being indicative of a survival signal. However, inhibition of CD84 activity with a blocking antibody or a blocking peptide derived from CD84, downregulated the expression of Bcl-2, thus inducing cell death. Therefore, the present findings set CD84 as a diagnostic marker for B-CLL and, being a regulator of B-CLL survival, as a target for the development of novel therapeutic modalities. Thus, according to one aspect of the present invention there is provided a method of diagnosing B-CLL in a subject in need thereof. The method comprising determining in a biological sample of the subject a level of CD84 isoform C (SEQ ID NO: 30), wherein an increase in said level of said CD84 isoform C (SEQ ID NO: 30) beyond a predetermined threshold with respect to a level of said CD84 in a biological sample from a healthy individual is indicative of the B-CLL.

As used herein the term "diagnosis" or "diagnosing" refers to classifying a pathology (e.g., cancer, e.g., leukemia e.g., chronic lymphoid leukemia (CLL) e.g., B-CLL).

According to this aspect of the invention, the term "subject" or "subject in need thereof" refers to a mammalian e.g., human subject having a routine check-up or screen for the pathology, as well as to a subject who is at risk of having the pathology such as due to family history, environmental factors and/or a subject who exhibits suspicious clinical signs of the pathology. Some clinical signs of B-CLL include but are not limited to predisposition to repeated infections such as pneumonia, herpes simplex labialis, and herpes zoster; enlarged lymph nodes; early satiety and/or abdominal discomfort which can be related to an enlarged spleen; mucocutaneous bleeding and/or petechiae which may be due to thrombocytopenia; tiredness and fatigue due to secondary to anemia; fevers, chills, and night sweats and weight loss; autoimmune hemolytic anemia.

As used herein the term "B-CLL" or "CLL" refers to an abnormal neoplastic proliferation of B-cells. CLL is considered to be identical to a disease called small lymphocytic lymphoma (SLL), a type of non-Hodgkin's lymphoma which presents primarily in the lymph nodes. The World Health Organization considers CLL and SLL to present different stages of the same disease [Chiorazzi N, Rai K R, Ferrarini M (2005). "Chronic lymphocytic leukemia". N. Engl. J. Med. 352 (8): 804-15].

As used herein the phrase "CD84 isoform C" refers to the isoform of CD84 which is assigned with Accession Numbers AF054815.1 NP_003865.1 (NM 003874, Q9UIB8-3). SEQ ID NOs: 29, 30

Examples of "biological samples" include but are not limited to whole blood, serum, plasma, cerebrospinal fluid, urine, lymph fluids, and various external secretions of the respiratory, intestinal and genitourinary tracts, tears, saliva, milk as well as white blood cells, tissues, cell culture e.g., primary culture. According to a specific embodiment, the biological sample comprises B cells.

B-CLL cells can be obtained from the blood, the bone marrow, the spleen, and/or the lymph nodes.

CD84 isoform C level can be determined at the protein level (level of expression and/or activity) or at the mRNA level (e.g., RT-PCR, real-time PCR etc.).

Following is a non-limiting list of examples of methods of determining a level of CD84C.

Enzyme Linked Immunosorbent Assay (ELISA):

This method involves a reaction between an enzyme and a substrate. A biological sample which comprises CD84C is put in a microwell dish. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot:

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-Immunoassay (RIA):

In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence Activated Cell Sorting (FACS):

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical Analysis:

This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

RT-PCR Analysis:

This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

Exemplary antibodies and assays that may be used to detect CD84C and further markers of the present invention are further described in the Examples section herein below.

As mentioned an increase in the level of the CD84C beyond a predetermined threshold with respect to the level of same in a similar sample from a healthy individual is indicative of the disease (e.g., B-CLL).

As used herein, the phrase "biological sample from a healthy individual" refers to an unaffected control sample taken from a healthy subject (known not to have B-CLL) or from the same subject prior to the onset of the B-CLL (i.e., healthy). Since biological characteristics depend on, amongst other things, species and age, it is preferable that the control saliva come from a subject of the same species, age. Alternatively, control data may be taken from databases and literature. It will be appreciated that the control sample may also be taken from the diseased subject at a particular time-point, in order to analyze the progression (i.e., monitoring) of the disease.

The term "increase" according to specific embodiment should be statistically significant.

Once diagnosis is made, the subject may be informed of the disease I.e., presence or absence of same and potetntial therapies for B-CLL.

To improve assay sensitivity, the method may further comprise corroborating the diagnosis using a diagnostic assay selected from surface marker expression distinctive of said CD84 isoform c, karyotype analysis and germline mutations.

Following is a non-limiting list of such assays/markers which can be used to corroborate the diagnosis of B-CLL.

Cell surface markers—B-CLL lymphocytes typically show B-cell surface antigens, as demonstrated by CD19, CD20, CD21, and CD23 monoclonal antibodies. In addition, they express CD5, which is more typically found on T cells. Because normal $CD5^+$ B cells are present in the mantle zone (MZ) of lymphoid follicles, B-CLL is most likely a malignancy of an MZ-based subpopulation of anergic self-reactive cells devoted to the production of polyreactive natural autoantibodies. B-CLL cells express extremely low levels of surface membrane immunoglobulin, most often immunoglobulin M (IgM) or IgM/IgD and IgD. Additionally, they also express extremely low levels of a single immunoglobulin light chain (kappa or lambda).

Genetic analysis—An abnormal karyotype is observed in the majority of patients with CLL. The most common abnormality is deletion of 13q, which occurs in more than 50% of patients. Individuals showing 13q14 abnormalities have a relatively benign disease that usually manifests as stable or slowly progressive isolated lymphocytosis.

The presence of trisomy 12, which is observed in 15% of patients, is associated with atypical morphology and progressive disease. Deletion in the short arm of chromosome 17 has been associated with rapid progression, short remission, and decreased overall survival in CLL. 17p13 deletions are associated with loss of function of the tumor suppressor gene p53. Deletions of bands 11q22-q23, observed in 19% of patients, are associated with extensive lymph node involvement, aggressive disease, and shorter survival.

More sensitive techniques have demonstrated abnormalities of chromosome 12. Forty to 50% of patients demonstrate no chromosomal abnormalities on conventional cytogenetic studies. However, 80% of patients will have abnormalities detectable by fluorescence in situ hybridization (FISH). Approximately 2-5% of patients with B-CLL exhibit a T-cell phenotype.

Investigations have also identified a number of high-risk genetic features and markers that include germline immunoglobulin variable heavy chain ($IgV_H$), $IgV_H$ V3-21 gene usage, increased CD38 expression, increased Zap70 expression, elevated serum beta-2-microglobulin levels, increased serum thymidine kinase activity, short lymphocyte doubling time (<6 mo), and increased serum levels of soluble CD23. These features have been associated with rapid progression, short remission, resistance to treatment, and shortened overall survival in patients with B-CLL.

Germline mutations—Germline $IgV_H$ has been shown to indicate a poor prognosis. Studies have shown that these patients also have earlier progression of B-CLL after treatment with chemotherapy. The use of certain $IgV_H$ genes, V3-21, have also been associated with poor prognosis regardless of $IgV_H$ mutational status.

The present inventors have also identified CD84 as an important survival factor on B-CLL and as such as a target for therapeutic intervention.

Thus, according to another aspect of the invention there is provided a use of an agent which decreases activity or expression of CD84 in the manufacture of a medicament for treating B-CLL.

According to yet another aspect of the invention there is provided a use of an agent which decreases activity or expression of CD84 for treating B-CLL.

According to still another aspect of the invention there is provided a method of inducing apoptosis in B cells of a subject having B-CLL, the method comprising administering to the subject a therapeutically effective amount of an agent which decreases activity or expression of CD84, thereby inducing apoptosis in B cells of the subject.

According to still another aspect of the invention there is provided a method of treating B-CLL in a subject in need thereof, the method comprising administering to the subject a therapeutically effective amount of an agent which decreases activity or expression of CD84, thereby treating B-CLL.

According to a therapeutic aspect of the invention the subject is diagnosed with B-CLL.

CD84 refers to an expressed isoform of the CD84 gene. Examples include but are not limited to Q9UIB8-1, Q9UIB8-2, Q9UIB8-3, Q9UIB8-4, Q9UIB8-5, Q9UIB8-6 and Q9UIB8-7. According to a specific embodiment of this aspect of the present invention down regulation of CD84 relates to all CD84 isoforms. To this end, agents which recognize all the isoforms of CD84 (i.e., pan CD84) are preferably used.

Thus, downregulation of CD84 can be effected on the genomic and/or the transcript level using a variety of molecules which interfere with transcription and/or translation (e.g., antisense, siRNA, Ribozyme, DNAzyme), or on the protein level using e.g., antagonists, enzymes that cleave the polypeptide and the like.

Following is a list of agents capable of downregulating expression level and/or activity of CD84.

One example, of an agent capable of downregulating a CD84 a CDR-containing polypeptide such as an antibody or antibody fragment capable of specifically binding CD84. Preferably, the antibody specifically binds at least one epitope of an extracellular portion of CD84 and neutralizes/blocks its activity such as by interfering with its homophilic interactions.

Such a CDR-containing polypeptide (e.g., antibody) can be produced from the hyridoma that has been deposited at the CNCN Pateur Institut on Sep. 23, 2009 under the deposit number CNCM I-4228 (F8).

As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab') .sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10,: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Another molecule which can be used to downregulate CD84 activity is a non-functional form of CD84 which binds CD84 but inhibits it's signaling activity such as by inhibiting its homophilic interactions.

Thus, the present teachings further provide for an isolated polypeptide which comprises an amino acid sequence of a soluble CD84 (i.e., non-membrane bound), wherein the soluble CD84 binds CD84 expressed on B cells (e.g., with a binding affinity of at least $10^{-5}$ nM) and inhibits its homophilic interactions.

Due to its inherent affinity towards the extracellular portion of CD84, the soluble CD84 agent described herein can be also utilized in the above-described diagnostic aspects, such as by conjugating to same an identifiable moiety (e.g., fluorescent protein, alkaline phosphatase, myc/his tag, beta galactosidase and the like).

According to a specific embodiment, the soluble CD84 comprises an extracellullar domain of CD84 and is devoid of a transmembrane domain of CD84.

According to a specific embodiment, the soluble CD84 is fused to a moiety for increasing solubility of the soluble CD84.

According to a specific embodiment, the moiety for increasing solubility of the soluble CD84 is a heterologous amino acid sequence or a chemical moiety such as PEG and the like.

As used herein the phrase "heterologous amino acid sequence" refers to an amino acid sequence which does not endogenously form a part of the CD84 amino acid sequence. Preferably, the heterologous amino acid sequence does not down-regulate the biological activity (e.g. apoptotic) of the soluble CD84 polypeptide.

The heterologous amino acid sequence may thus serve to ensure stability of the soluble CD84 of the present invention without compromising its activity. For example, the heterologous polypeptide may increase the half-life of the soluble CD84 molecule in the serum. Examples of heterologous amino acid sequences that may be used in accordance with the teachings of the present invention include, but are not limited to, immunoglobulin, galactosidase, glucuronidase, glutathione-S-transferase (GST), carboxy terminal peptide (CTP) from chorionic gonadotrophin (CG) and chloramphenicol acetyltransferase (CAT) [see for example Suzuki et al., supra; and U.S. Publication No. 20030171551].

The exact site at which fusion (conjugation) between the moiety for increasing solubility and the CD84 amino acid sequence is not critical. Generally the moiety for increasing solubility is localized at the amino- or carboxyl-terminus (n-ter or c-ter, respectively) of the CD84 polypeptide of the present invention. Particular sites are well known in the art and may be selected in order to optimize the biological activity, secretion or binding characteristics of the chimeric molecules of this aspect of the present invention.

The heterologous amino acid sequence may be attached to the CD84 amino acid sequence by any of peptide or non-peptide bond. Attachment of the CD84 amino acid sequence to the heterologous amino acid sequence may be effected by direct covalent bonding (peptide bond or a substituted peptide bond) or indirect binding such as by the use of a linker having functional groups. Functional groups include, without limitation, a free carboxylic acid (C(=O)OH), a free amino group (NH$_2$), an ester group (C(=O)OR, where R is alkyl, cycloalkyl or aryl), an acyl halide group (C(=O)A, where A is fluoride, chloride, bromide or iodide), a halide (fluoride, chloride, bromide or iodide), a hydroxyl group (OH), a thiol group (SH), a nitrile group (C≡N), a free C-carbamic group (NR"—C(=O)—OR', where each of R' and R" is independently hydrogen, alkyl, cycloalkyl or aryl).

An example of a heterologous amino acid sequence which may be used in accordance with this aspect of the present invention is an immunoglobulin amino acid sequence, such as the hinge and Fc regions of an immunoglobulin heavy domain (see U.S. Pat. No. 6,777,196). The immunoglobulin moiety in the chimeras of this aspect of the present invention may be obtained from IgG1, IgG2, IgG3 or IgG4 subtypes, IgA, IgE, IgD or IgM, as further discussed hereinbelow. Chimeras constructed from a receptor sequence linked to an appropriate immunoglobulin constant domain sequence (immunoadhesins) are known in the art. Immunoadhesins reported in the literature include fusions of the T cell receptor [Gascoigne et al., Proc. Natl. Acad. Sci. USA, 84: 2936-2940 (1987)]; CD4 [Capon et al., Nature 337: 525-531 (1989); Traunecker et al., Nature, 339: 68-70 (1989); Zettmeissl et al., DNA Cell Biol. USA, 9: 347-353 (1990); Byrn et al., Nature, 344: 667-670 (1990)]; L-selectin (homing receptor) [(Watson et al., J. Cell. Biol., 110:2221-2229 (1990); Watson et al., Nature, 349: 164-167 (1991)]; CD44 [Aruffo et al., Cell, 61: 1303-1313 (1990)]; CD28 and B7 (Linsley et al., J. Exp. Med., 173: 721-730(1991)]; CTLA-4 [Lisley et al., J. Exp. Med. 174: 561-569 (1991)]; CD22 [Stamenkovic et al., Cell, 66:1133-1144 (1991)]; TNF receptor [Ashkenazi et al., Proc. Natl. Acad. Sci. USA, 88: 10535-10539 (1991); Lesslauer et al., Eur. J. Immunol., 27: 2883-2886 (1991); Peppel et al., J. Exp. Med., 174:1483-1489 (1991)]; NP receptors [Bennett et al., J. Biol. Chem. 266:23060-23067 (1991)]; and IgE receptor a [Ridgway et al., J. Cell. Biol., 1 15: abstr. 1448 (1991)].

Typically, in such fusions the chimeric molecule will retain at least functionally active hinge and CH2 and CH3 domains of the constant region of an immunoglobulin heavy chain. Fusions can also be generated to the C-terminus of the Fc portion of a constant domain, or immediately N-terminal to the CH1 of the heavy chain or the corresponding region of the light chain.

According to a presently exemplified embodiment, the soluble CD84 is as set forth in SEQ ID NO: 2.

The present invention further provides for an isolated (from the natural environment) polynucleotide which comprises a nucleic acid sequence encoding a soluble CD84 as described above.

In order to express the polynucleotide it is preferably ligated into a nucleic acid expression construct under the control of a cis-regulatory element e.g., promoter.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter (Zabala M, et al., Cancer Res. 2004, 64(8): 2799-804).

The nucleic acid construct (also referred to herein as an "expression vector") of the present invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of the present invention typically includes a signal sequence for secretion of the peptide from a host cell in which it is placed. Preferably the signal sequence for this purpose is a mammalian signal sequence or the signal sequence of the polypeptide variants of the present invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of CD84 mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMT010/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Another agent capable of downregulating a CD84 is a small interfering RNA (siRNA) molecule. RNA interference is a two step process. The first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 by duplexes (siRNA), each with 2-nucleotide 3' overhangs [Hutvagner and Zamore Curr. Opin. Genetics and Development 12:225-232 (2002); and Bernstein Nature 409: 363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the CD84 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs)

are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Another agent capable of downregulating a CD84 is a DNAzyme molecule capable of specifically cleaving an mRNA transcript or DNA sequence of the CD84. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther www.asgt.org). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of a CD84 can also be effected by using an antisense polynucleotide capable of specifically hybridizing with an mRNA transcript encoding the CD84.

Design of antisense molecules which can be used to efficiently downregulate a CD84 must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Another agent capable of downregulating a CD84 is a ribozyme molecule capable of specifically cleaving an mRNA transcript encoding a CD84. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

The agents of the present invention can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accountable for the biological effect (i.e., down regulation in CD84 activity or expression).

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

The term "tissue" refers to part of an organism consisting of an aggregate of cells having a similar structure and/or a common function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., B-CLL) or prolong the survival of the subject being treated. In a specific embodiment, the therapeutically effective amount is sufficient to induce B-CLL apoptosis.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

A B-CLL animal model such as the NOD-SCID mouse chimera as described previously [Shimoni A, Marcus H, Canaan A, et al. A model for human B-chronic lymphocytic leukemia in human/mouse radiation chimera: evidence for tumor-mediated suppression of antibody production in low-stage disease. Blood. 1997; 89:2210-2218], can be used to determine therapeutic efficacy of the agents of the present invention in vivo. Human peripheral blood mononuclear cells from B-CLL patients at different stages of the disease are transferred by intraperitoneal injection. This system supports long term survival of the human tumor cells. Chimeric mice are treated with the agents of the present invention for different periods of time, and the effect on grafting of the cells and survival is then assessed.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide (tissue) levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

To improve therapeutic efficacy, agents of the present invention can be further administered along with conventional therapy for B-CLL such as chemotherapy, radiotherapy, biological therapy e.g., immunotherapy or bone marrow transplantation.

Following is a non-limiting list of examples of conventional therapies for B-CLL.

Purine analogs—fludarabine or chlorambucil are generally used in this category of treatments.

Monoclonal antibodies—Monoclonal antibodies such as alemtuzumab (directed against CD52) and rituximab (directed against CD20) are generally used in this category of treatments.

Combination chemotherapy—Combination chemotherapy options are typically used in newly-diagnosed and relapsed CLL. Recently, randomized trials have shown that combinations of purine analogues (fludarabine) with alkylating agents (cyclophosphamide) produce higher response rates and a longer progression-free survival than single agents: e.g., FC (fludarabine with cyclophosphamide); FR (fludarabine with rituximab); FCR (fludarabine, cyclophosphamide, and rituximab); CHOP (cyclophosphamide, doxorubicin, vincristine and prednisolone).

Allogeneic bone marrow (stem cell) transplantation—rarely used as a first-line treatment for CLL due to its risk. There is increasing interest in the use of reduced intensity allogeneic stem cell transplantation, which offers the prospect of cure for selected patients with a suitable donor.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, C T (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Procedures

Generation of CD84-ECD

For generating a DNA fragment encoding for the extracellular domain of CD84 (CD84-ECD), the PCR was performed according to Tables 1 and 2. The primers contained overhangs with recognition sites for EcoR I and BamH I restriction endonucleases.

TABLE 1

Formulation for preparative PCR ([50] µL)

| [2 pt] reaction component | amount |
|---|---|
| 10 µl Pfu buffer | [5] µL |
| dNTP mix [10]mM 10 mM | [1] µL |
| 5' primer, 5'BamH1CD84 | [0.2] µL ([12]pmol) |
| 3' primer, 3'EcoR1CD84 | [0.2] µL ([12]pmol) |
| Pfu Polymerase | [1] µL |
| water | [41.6] µL |

TABLE 2

Cycling parameters for preparative PCR ([50] μL)

| [2 pt] step nr. | temperature | time period | process |
|---|---|---|---|
| 1. | [95] C. | [10] min | initial denaturation |
| 2. | [95] C. | [1] min | melting |
| 3. | [51] C. | [30] s | annealing |
| 4. | [72] C. | [70] s | extension |
| 5. | [72] C. | [8] min | final extension |
| 6. | [8] C. | | |

Steps 2 through 4 were repeated 39 times

After purification of the CD84-ECD PCR product, the restriction enzymes EcoR I and BamH I were used to digest the pEF4 vector and the PCR product itself to yield complementary, cohesive ends. Therefore, the complete purified CD84-ECD PCR product ([30] μL) was put to reaction with 20 units of EcoR I and BamH I ([1] μL each), [5] μL 10 μL buffer for EcoR I and water to make a final volume of [50] μL. The formulation was incubated overnight at [37]° C. and then purified again. [3]πμg of the pEF4-myc/His plasmid were digested analogously. Control reactions each with only one of the two enzymes were performed and analyzed by agarose gel electrophoresis. The digested and purified CD84-ECD insert and the digested and purified pEF4-myc/His vector were ligated using a molar ratio of 1:5 between vector and insert. The mixture was incubated overnight at [15]° C. and directly used for transformation of DH5 alpha bacteria. Positive transformants containing the CD84ECD were identified using colony PCR, using the primers for the CD84ECD. CD84-ECD was subcloned from pEF4-my/His into pET21a vector by restriction with EcoRI and BamHI. Positive coloning was confirmed by colony PCR.

Site Directed Mutagenesis

The Stratagene QuickChange Site-directed Mutagenesis Kit was used, following the manufacturer's instructions. The following tyrosine mutants were derived from the CD84-full construct:
1. Y262F
2. Y262F, Y299F
3. Y279F
4. Y279F, Y324F Primers used for cloning are listed below RNA Isolation RNA was isolated using the TRI Reagent MRC (molecular research center, inc) according to the manufacturers instructions.

cDNA Synthesis

In order to synthesize cDNA from isolated RNA (see above), for each sample [1] μg of RNA was mixed with [1] μL oligo-dT primer and made up with water to a volume of [16] μL. The mixture was incubated at [70]° C. for [5] min and then chilled for [2] min on ice. [12] μL of the following solution was added, followed by incubation for [1] at [42]° C.:

TABLE 3

| [5] μL | RT buffer |
|---|---|
| [3] μL | [0.1]M DTT |
| [2] μL | dNTPs [10] mM |
| [0.7] μL | dHO |
| [0.3] μL | HPRI RNAsin |
| [1] μL | MMLV Superscript II RT |

Analytical PCR

Analytical PCR was performed using a Taq 2ReadyMix (Bio Lab), which contains all necessary components, beside primers and template. Used primers are listed below with their respective annealing temperatures. The typical number of cycles was 33-39, dependent on the sample and the gene. Actin was used as a reference gene, and a control PCR without template was performed in parallel as a control for contamination. The PCR products were evaluated by analytical agarose gel electrophoresis.

Analysis of Different CD84 Isoforms

The different isoforms of CD84 were analyzed by the system established by Palou et al. (2000) Palou, E., Pirotto, F., Solé, J., Freed, J. H., Peral, B., Vilardell, C., Vilella, R., Vives, J. & Gayá, A. (2000), 'Genomic characterization of CD84 reveals the existence of five isoforms differing in their cytoplasmic domains', *Tissue Antigens* 55(2), 118-27, which is hereby incorporated by reference in it's entirety.

All the five isoforms of CD84 share the same sequence of the extracellular part, but differ in their intracellular sequence. More precisely, CD84a, b, c and d have a similar nucleotide sequence, besides a short "spacer" of different length in their membrane-proximal cytoplasmic part.

By using a pair of primers framing this variable part (the 5' primer in the extracellular, the 3' primer in the intracellular part), one single PCR yields fragments of different length for these isoforms. Due to a cytoplasmic sequence difference from the other isoforms, CD84e can be specifically analyzed by a pair of primers, which utilizes the same extracellular primer as before, but an individual primer for the intracellular sequence.

TABLE 4

Isoforms of CD84 and their accession numbers

| Denomination | GenBank accession number (mRNA protein) (UniProtKB/Swiss-Prot identifier)/SEQ ID NO of nucleic acids and proteins | length (aa) |
|---|---|---|
| CD84a | AF054816 AAF21722.1 (Q9UIB8-1/25, 26) | 345 |
| CD84b | Y12632 CAA73181.1 (Q9UIB8-2/27, 28) | 339 |
| CD84c | AF054815.1 NP_003865.1 (Q9UIB8-3/29, 30) | 328 |
| CD84d | AF054817 AAF21723.1 (Q9UIB8-5/31, 32) | 272 |
| CD84e | U96627 AAD04232.1 (Q9UIB8-4/33, 34) | 280 |

Primers

Primers for Each Isoform

```
5'CD84d (SEQ ID NO: 3)   TACATGCCTTAGGTCCGA
NM_003874.2

3'CD84d (SEQ ID NO: 4)   GAGGGAAGCACCTTGT
NM_003874.2

5'CD84all (SEQ ID NO:    TGCCTGCAAACCTGGCCGGAAGCA
5) all CD84 constructs
```

-continued

| | | |
|---|---|---|
| 3'CD84all (SEQ ID NO: 6) all CD84 constructs | TGCAGGTTGTAGCGCTTGGTGGTGGT | |
| 5'SAP (SEQ ID NO: 7) 56_C NM_002351.3 | AGCGTGCCAGGCGTGTACTG | |
| 3'SAP (SEQ ID NO: 8) 56_C NM_002351.3 | ACACCAGCCAACTTCCCACCA | |
| 5'EAT2 (SEQ ID NO: 9) NM_053282 | GCTCAAGGAAGGGGTGGATGGC | |
| 3'EAT2 (SEQ ID NO: 10) NM_053282 | TCTGGTGCTGGTGGGCAGAAC | |
| 3'Bcl2 (SEQ ID NO: 11) NM_000633.2 | ACAAGTGAAGTCAACATGCC | |
| 5'Bcl2 (SEQ ID NO: 12) NM_000633.2 | GCAAGTGAATGAACACCTTC | |
| Actin: 5' (SEQ ID NO: 13) | TGAAGTGTGACGTGGACATCCG | |
| 3' (SEQ ID NO: 14) | GCTGTCACCTTCACCGTTCCAG | |

Primers for the Tyrosine Mutations

| | |
|---|---|
| 5'Y262 (SEQ ID NO: 15) | GATGCTGCCTCAAAGAAAACCATATTCACATATATCATGGCTTC |
| 3'Y262 (SEQ ID NO: 16) | GAAGCCATGATATATGTGAATATGGTTTTCTTTGAGGCAGCATC |
| 5'Y299 (SEQ ID NO: 17) | GAGCCAGTGAACACAGTTTTTTCCGAAGTGCAGT |
| 3'Y299 (SEQ ID NO: 18) | ACTGCACTTCGGAAAAAACTGTGTTCACTGGCTC |
| 5'Y279 (SEQ ID NO: 19) | GCCAGCAGAGTCCAGAATCTTTGATGAAATCCTG |
| 3'Y279 (SEQ ID NO: 20) | CAGGATTTCATCAAAGATTCTGGACTCTGCTGGC |
| 5'Y324 (SEQ ID NO: 21) | ACTCCTGGGACTTCAAGCTTTGAAATTGTGATCG |
| 3'Y324 (SEQ ID NO: 22) | CGATCACAATTTCAAAGCTTGAAGTCCCAGGAGGT |

Primers Sequence for the CD84-ECD

| | |
|---|---|
| 5'BamH1CD84 (SEQ ID NO: 23) | CGTCGGATCCATGGCTCAGCACCAC |
| 3'EcoR1CD84 (SEQ ID NO: 24) | TAGCGAATTCACGGAAGCCCATTGC |

Antibodies
  anti-Bcl-2 (C-2; Santa Cruz)
  anti-tubulin antibody (Sigma),
  peroxidase-conjugated anti-mouse (Jackson Labs).
  CD84 activating (ab3202 abcam) antiFab (Jackson Labs).
  CD84 blocking (CD84.1.21 Biolegend)
  CD84 for IP (152-1DS santa cruz)
  Generation of Stably CD84-Transfected HEK 293T Cells
  HEK 293T cells were stably transfected with the CD84-full construct, which promotes the expression of myc- and His-tagged CD84, isoform c. Prior to transfection the vector was linearized to prevent integration in a way that would disrupt the CD84 gene. The pEF4 plasmid contains the Zeocin resistance gene which was used for selection of stably transfected cells. Mammalian cells exhibit a wide range of succesibilty to Zeocin. Hence, the first step in the generation of a stable cell line is to determine the minimum concentration of Zeocin, required to kill the untransfected host cell line. Therefore, HEK 293T cells were seeded on 6-well plates to yield [25]% confluency. After [24] h, the medium was replaced with medium containing varying concentrations of Zeocin: 0, 150, 300, 500, 700 and [1000] µgmL. The selective medium was replenished every 3-4 days and the cells were observed for survival over time. The concentration which killed the majority and inhibited growth of the cells in 12 days was selected for the following selection procedure. Zeocin-sensitive HEK 293T can be easily differentiated from resistant cells by their vast increase in size and abnormal cell shape.

Transfection and Protein Expression of Secreted CD84-ECD

For expression and secretion of CD84-ECD protein the following protocol has proven to be advantageous. Sixteen to twenty hours before transfection, HEK 293T cells were plated in 175 cm cell culture flasks to a final confluency of [75]%. A minimal amount of [30] mL complete DMEM medium and [3] mL of DNA precipitate-containing solution was used for transfection. Sixteen to 24 hours after transfection, the medium was changed to serum-free DMEM for three to four days. This conditioned medium was collected, centrifugated at [4000] g for 2 hours to remove cells and debris, filtrated with a [0.2] µm filter unit and concentrated to a volume of [1] mL, using Vivaspin 20 sample concentrators. After addition of [1]% Protease Inhibitor Cocktail the solution was stored at [4]° C. for further use.

Detection of CD84 Surface Expression by Flow Cytometry

Surface expression of CD84 by stably transfected HEK 293T cells was detected by flow cytometry. Cells of a near-confluent [35] mm culture dish were collected without the use of trypsin. The cell suspension was divided into fractions of [200] µL in a 96-well plate, for the following treatments: cells without staining, cells incubated with secondary antibody and duplicates of cells incubated with primary and secondary antibody. The cells were pelletized by centrifugation at [300] g for 4 minutes and resuspended in PBS containing the primary anti-CD84 antibody with a dilution of 1:100. After incubation for 20 minutes at [4]° C., the cells were washed with PBS and resuspended in PBS containing the FITC-conjugated secondary anti-mouse antibody. Following incubation for 20 minutes at [4]° C., the cells were washed once more and resuspended in [300] µL PBS. The samples were analyzed using a Becton Dickinson (BD) FACSCalibur flow cytometer. The BD Cell Quest software was used for gating and analyzing the viable population of cells.

In Vitro Cross-Linking of CD84

In order to activate the downstream signaling cascade of CD84 in transiently transfected cells, the following steps were performed. HEK 293T cells were transfected with CD84-full plasmid in a 12-well cell culture dish, as described above, and [6] h post-transfection the medium was replenished. The cells were then incubated with [1.25] µL of Abcam anti-CD84 antibody for [30] min and subsequently with [0.5]

μL of the secondary anti-Fab antibody. For Western blot analysis, the cells were harvested [24] h after activation.

Co-Immunoprecipitation

The co-immuniprecipitation (co-IP) can be used to identify members of protein complexes. Therefore, [30] μL of protein-G sepharose beads were coated with [3] μg CD84 or IgG control antibody. HEK 293T cells were transfected in a [35] mm cell culture dish with [1] μg CD84-full and [1] μg CD74 plasmid, [24] h prior to harvest. The immuno-precipitate was prepared as follows:

The cells were harvested, the pellet was immediately frozen in liquid N, and then resuspended in [300] μL lysis buffer for IP. After incubation for [30] min on ice, the solution was centrifugated for [30] min at [18000] g and the supernatant was divided into two fractions: [30]μL (for use as a total protein sample) were mixed with [6] μL 5μ sample buffer with [1]% β-mercaptoethanol following incubation at [99]° C. for [10] min. The remaining lysate was incubated overnight with the coated beads under constant agitation. The beads were washed twice with IP solution 1 and once with IP solution 2. After complete removal of the supernatant, [35] μL sample buffer with β-mercaptoethanol were added to the precipitate. After mixing and brief centrifugation the supernatant was used for analysis by SDS-PAGE and Western blotting.

Protein Sample Preparation from HEK 293T Cells with RIPA

Cell culture medium was removed and the adherent cells were washed carefully with ice-cold PBS. The cells were detached, resuspended in 1 ml PBS, and pelleted at [300] g for [4] min. The supernatant was removed and the pellet was resuspended in the appropriate volume of RIPA buffer with [1]% protease inhibitors. A minimal volume of [100] μL per [10] cm growth area (average cell yield for a confluent [35] mm culture plate:) was used. The suspension was incubated on ice under periodic agitation for thirty minutes and then centrifugated at [18000] g for [30] min. Centrifugation was performed at [4]° C. The supernatant was transferred to a new tube and combined 1:5 with 5 μl sample buffer ([1]% β-mercaptoethanol). Afterwards, the solution was boiled for 10 minutes at [99]° C. and frozen at [−20]° C. until analysis by SDS-PAGE and Western blotting.

Protein Sample Preparation from HEK 293T Cells with Hot-SDS

Cells were washed, harvested and pelleted. The pellet was loosened by strong agitation and pre-heated ([99]° C.) Hot-SDS solution was added. A minimal volume of [100] μL per [10] cm growth area (average cell yield for a confluent [35] mm culture plate:) was used. The sample was boiled for [2] min at [99]° C. and then shock-frozen in liquid nitrogen for at least four minutes. Afterwards, the sample was boiled again for [2] min, subjected to sonication on ice and combined 1:5 with 5 μl sample buffer ([1]% β-mercaptoethanol)

Protein Purification from Conditioned Medium Using FLPC

Affinity chromatography is based on specific and reversible adsorption of a molecule to a matrix-bound binding partner. The nature of binding occurs either naturally (e.g., as for antigen—antibody) or can be genetically introduced to a protein, with specific "tags". A special group of affinity chromatography methods utilizes immobilized metal chelating groups: Multivalent transition metal ions are bound to the resin in a way that allows free coordinate bonds to interact with basic groups of proteins. The here used His-tag achieves such a strong complexation of Ni ions, which can be utilized for affinity chromatography, when using a resin with immobilized nickel ions. After adsorption of the protein to the column, it is washed and can eventually be eluted in high concentrations of imidazole, which competes with the His-tag for Ni-complexation and displaces the protein. Following purification, concentrated samples of each purification step and of the different peaks are typically analyzed by SDS-PAGE followed by Western Blotting and Coomassie staining of the gel.

Nickel Affinity Chromatography

In general a protein purification with Ni columns consisted of the following steps:
1. washing the column with water to remove residual ethanol from storrage
2. equilibration of the column with PBS containing [20] mM imidazole
3. loading of the solution which contains the His-tagged protein
4. washing the column with PBS containing [20] mM imidazole
5. eluting the protein with PBS containing [250] mM imidazole For each washing and equilibration step, a volume of at least 10 times of the column volume was used. If not noted otherwise, the flow rate was [5] mLmin. The protein was concentrated as described above (Transfection and protein expression of secreted CD84-ECD) and diluted 1:10 in PBS with [20] mM imidazole. The protein solution was applied to the equilibrated HisTrap HP [5] mL Ni sepharose column at flow rates between 1 and [3] mLmin. The column was washed with PBS containing [20] mM imidazole, which prevents unspecific binding of proteins rich in histidine. The elution of the protein was carried out using PBS, containing [250] mM imidazole. The applied ÄKTA Basic FPLC system allows for immediate monitoring of the eluate by means of absorption measurements of three different UV wavelengths, pH and conductance. This way, proper fractions could be taken "on-the-fly". The fractions of the presumptive protein peak were pooled, concentrated to a volume of 1-[2] mL using Vivaspin 20 sample concentrators and subjected to gel filtration as described (see below).

Size-Exclusion Chromatography

Size-exclusion chromatography, also known as gel filtration, separates molecules by their size and is based on the differential permeation of an analyte into a porous resin with controlled pore size. Large molecules, which are unable to penetrate the pores, elute concomitantly with the solvent front (exclusion volume). Smaller molecules infiltrate the pores and are retained. Thus, the smallest components have the longest detention time and are eluted last.

The pooled, concentrated fractions of the Ni affinitiy chromatography were loaded onto a 16/60 Superdex 200 column (preparation grade) by injection into the FPLC system. The proteins were eluted at a flow rate of [5] mLmin with PBS as the eluent. Fractions were collected according to the UV absorption and changes in pH of the eluate. After pooling and concentrating the different peak fractions, samples were analyzed by SDS-PAGE, followed by Western blotting and Coomassie staining. The protein concentration of the samples was determined by the Bradford assay.

Proteolytic Digestion and Protein Identification by ESI-MS/MS

In order to verify the identity of the CD84-ECD protein, the presumptive band of the Coomassie-stained gel was excised and analyzed by proteolytic digestion followed by electrospray ionization mass spectrometry. The procedure was carried out by the Biological Service Unit at the Weizmann Institute.

Example 1

Identification of CD84 Target Genes

The initial goal of the present study was to identify target genes of CD74 and their role in B-CLL cell survival, using cells obtained from patients at the Hematology Institute at the Kaplan Medical Center.

Identification of CD74 target genes—to this end, B-cells from B-CLL (also referred to as B-CLL cells) patients were incubated in the presence or absence of MIF (100 ng/ml), the Affymetrix GeneChip® expression analysis system was used to compare the expression patterns of RNA from these two populations. In this analysis, RNA from MIF-stimulated cells was compared to RNA derived from unstimulated cells. Many genes were found to be differentially expressed in these populations; one striking example was CD84, whose expression was markedly elevated in the MIF-induced B-CLL cells.

CD84 expression levels in B-CLL cells—CD84 cell surface expression levels were compared in circulating B-CLL cells to levels on normal circulating mature B cells. Purified B cells from healthy subjects as well as early- and advanced-stage B-CLL patients were analyzed by means of RT-PCR for the presence of CD84 mRNA (a segment common to all isoforms). As shown in FIG. 1A, low levels of CD84 mRNA were detected in normal B cells, while elevated levels of CD84 mRNA were observed in all the CLL patients, regardless of the stage of disease.

Next, flow cytometry (FACS) analysis was used to determine whether these elevated levels of CD84 were expressed on the cell surface of B-CLL cells. As shown in FIGS. 1B-C, higher levels of CD84 were expressed on the cell surface of all B-CLL cells, when compared to normal B cells. These results were uniformly seen in all the samples examined, regardless of the clinical parameters of the patients, including stage of the disease [either RAI or Binet, Cheson B D, Bennett J M, Greyer M, et al. National Cancer Institute-sponsored Working Group guidelines for chronic lymphocytic leukemia: revised guidelines for diagnosis and treatment. Blood. 1996; 87:4990-4997 (See Table 5, below)].

TABLE 5

| CD84 Expression levels as determined by FACS | |
|---|---|
| % of CD84 cell surface expression | |
| normal B cells | |
| normal | 14 |
| normal | 15 |
| CLL-B cells | |
| early | 76 |
| advanced | 58 |
| early | 79 |
| advanced | 83 |
| early | 87 |
| advanced | 66 |
| advanced | 71 |
| early | 73 |
| early | 81 |
| early | 71 |
| early | 81 |
| advanced | 71 |
| advanced | 82 |
| av (CLL) | 75.3 |
| SD (CLL) | 7 |
| Fold of CD84 expression following MIF stimulation | |
| advanced | 1.3 |
| advanced | 1.8 |
| early | 1.5 |
| early | 1.3 |
| advanced | 1.4 |
| early | 1.6 |
| advanced | 1.6 |
| advanced | 1.4 |
| advanced | 1.5 |
| av | 1.5 |
| sd | 0.15 |

Figures 2A, 2B:
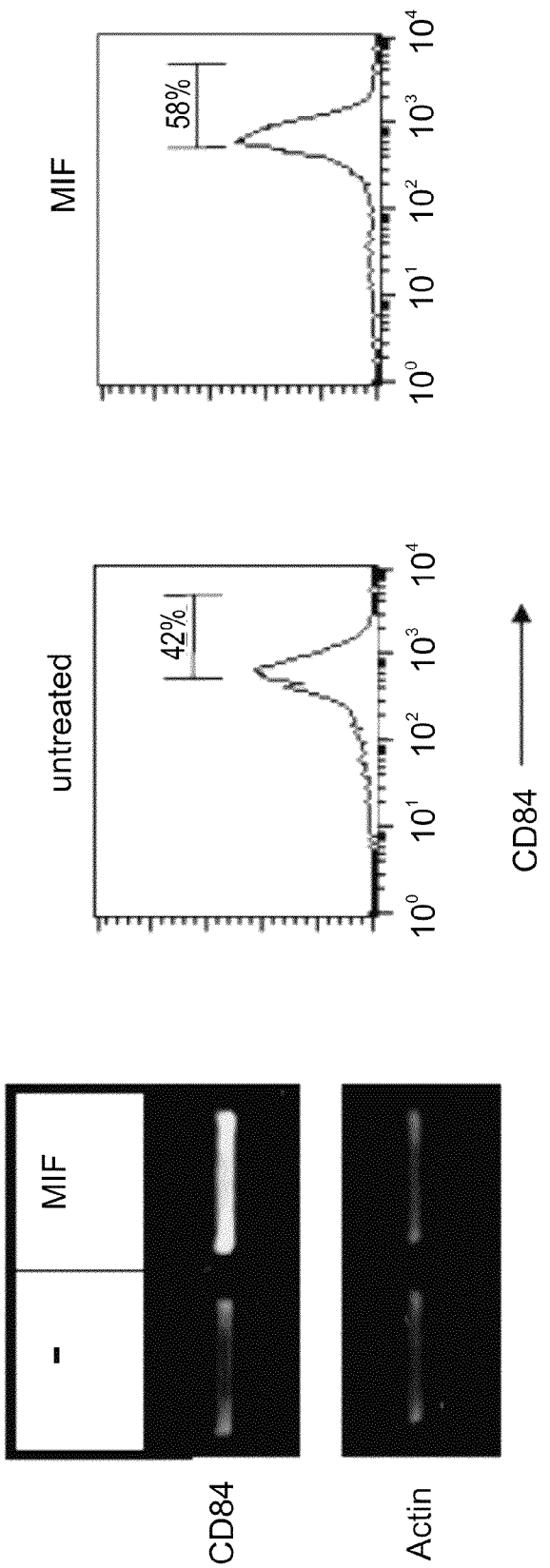

CD84 is modulated by CD74—To verify that CD84 expression is indeed modulated by CD74, the transcript level of CD84 were analyzed by RT-PCR in MIF-stimulated B-CLL B-cells compared to unstimulated cells. As seen in FIG. 2A, CD74 indeed dramatically elevated CD84 mRNA levels. This elevation also resulted in an increase in its cell surface expression (FIGS. 2B-C).

ISO-1 is a non-toxic inhibitor of MIF that binds to bioactive MIF at its N-terminal tautomerase site [Dios A, Mitchell R A, Aljabari B, et al Inhibition of MIF bioactivity by rational design of pharmacological inhibitors of MIF tautomerase activity. J Med Chem. (2002); 45:2410-2416]. To determine whether MIF secreted from B-CLL regulates CD84 expression, the mRNA levels of MIF were analyzed in cells incubated in the presence or absence of this inhibitor. Furthermore, ISO-1 significantly downregulated CD84 mRNA levels (FIG. 2C) and cell surface expression levels (FIG. 2D), showing that MIF regulates B-CLL CD84 expression levels.

Example 2

Activation of Cell Surface CD84 in B-CLL Cells Initiates a Survival Cascade in B-CLL and HEK 293 Cells To determine whether cell surface CD84 transmits a signal that results in activation of downstream signaling cascades in B-CLL cells, CD84 was cross-linked with anti-CD84 or control IgG1 antibody mAb (Abcam, Tangye S G, van de Weerdt B C M, Avery D T, Hodgkin P D. CD84 is up-regulated on a major population of human memory B cells and recruits the SH2 domain containing proteins SAP and EAT-2. European Journal of Immunology. 2002; 32:1640-1649). The cells were then washed, and bound mAb was cross-linked with F(ab')$_2$ goat anti-mouse Ig. CD84 tyrosine phosphorylation was determined following its ligation. As shown in FIG. 3A, CD84 ligation induces its own tyrosine phosphorylation. Next the CD84 downstream cascade was followed, and especially its role in B-CLL survival. It was previously demonstrated that stimulation of cell surface CD74 on B-CLL cells results in elevation of IL-8 and Bcl-2 expression (Binsky I, Haran M, Starlets D, et al. IL-8 secreted in a macrophage migration-inhibitory factor- and CD74-dependent manner regulates B cell chronic lymphocytic leukemia survival. Proc Natl Acad Sci USA. 2007; 104:13408-13413). Therefore, IL-8 and Bcl-2 mRNA levels were determined following CD84 stimulation. B-CLL were incubated in the presence or absence of anti-CD84, and the mRNA levels of IL-8 and Bcl-2, which were previously shown to regulate B-CLL survival was analyzed. As shown in FIG. 3B, anti-CD84 stimulation upregulated IL-8 and Bcl-2 mRNA levels, and Bcl-2 protein levels indicating that activation of B-CLL CD84 initiates a survival cascade.

To determine whether the human CD84 (hCD84) survival cascade is specific to B-CLL cells, or whether this molecule can trigger a similar cascade in additional cells including normal cells, CD84 signaling was determined in HEK 293-transfected cells which express low levels of endogenous CD84 resulting in a C-terminal c-myc epitope-tagged version of CD84. The human CD84 isoform C (the major isoform found in B-CLL cells) was cloned to pEF4/Myc-His vector construct. To reveal whether hCD84 induces a survival cascade in HEK 293 cells, its effect on the transcription of Bcl-2 was examined Full-length hCD84 indeed induced Bcl-2 transcription in these cells. Moreover, ligation of cell surface hCD84 with an activating anti-CD84 antibody significantly elevated the levels of Bcl-2 transcription in HEK 293 cells (FIG. 4 A). This elevation was a specific response to CD84 stimulation and did not occur in cells transfected with an empty construct (FIG. 4B). Thus, similar to the pathway that was demonstrated in B-CLL cells, CD84 activates a cell survival pathway resulting in Bcl-2 transcription in 293 cells.

To directly demonstrate that stimulation with anti-CD84 agonistic antibody induces B-CLL cell survival, B-CLL cells were incubated in the presence or absence of anti-CD84 mAb and a control antibody (IgG1) for 24 h. The cells were then analyzed for apoptosis by Annexin staining, as previously described (Gore Y, Starlets D, Maharshak N, et al. Macrophage migration inhibitory factor (MIF) induces B cell survival by activation of a CD74/CD44 receptor complex. J Biol Chem. 2008; 283:2784-2792). As shown in FIG. 5, CD84 stimulation reduced the percentage of Annexin-positive cells. Thus, it is suggested that CD74 regulates B-CLL survival by upregulating CD84 cell surface expression levels. Activation of CD84 induces expression of Bcl-2, which regulates B-CLL survival.

Example 3

Expression of CD84 Isoforms in B-CLL

There are at least five different isoforms of CD84. In order to determine whether those isoforms might have distinct functions and a specific isoform might play a role in B-CLL cells, the expression pattern of the various isoforms in B-CLL cells was analyzed. To follow the CD84 mRNA isoforms on the mRNA level, a semi-quantitaitve RT-PCR approach was chosen, using oligonucleotides designed by \citen{palou_genomic__2000}.

The primer pairs 5'CD84comu/3'CD84alt2 flank a region starting in the extracellular part and ending in the last exon, which is common to all isoforms except CD84e. Therefore, this primer pair generates PCR products for all isoforms except CD84e, which can be analyzed by the primer pair 5'CD84comu/3'CD84orig. To minimize unspecific PCR products, the annealing temperature was optimized and increased from 60 to 64° C. Another primer pair, specific for CD84d was designed. mRNA from 12 different B-CLL patients were compared to mRNA from healthy persons. FIGS. 6A-B the result of exemplary experiments.

In all tested samples (13 patients) CD84c was the dominate isoform in healthy, early and advanced stage B-CLL patients. In all the samples analyzed, there was no clear correlation in CD84d and CD83e mRNA levels in control and B-CLL samples.

Example 4

CD84 Tyrosine Signaling Motifs as Mediators of the Survival Signal

To analyze CD84 signaling cascade in HEK 293T cells, tyrosines involved in the survival cascade were first analyzed. Therefore, point mutants in the four tyrosine motifs of CD84c were designed. Two of these mutated tyrosines (Y262 and Y299) are consensus motifs for SH2-interactions with SAP/EAT2/SHP-2. Little is known about the other two SH2-interacting motifs (Y279 and Y324), from which Y324 resembles an ITIM motif \citep{vila_the__2007}. As shown in FIG. 7, two different mutants, one missing Y262 and Y299 and the other one missing Y279 and Y324 were generated.

To determine which motifs regulate Bcl-2 expression, HEK 293T cells were transiently transfected with CD84-full, CD84 [Y262F, Y299F], CD84 [Y279F, Y324] and empty vector as a control. The cells were plated to give a confluence of about 70% in order to achieve detectable changes in the expression of Bcl-2. Following 24-40 h the cells were harvested and the expression of the constructs was verified by probing with anti-myc antibody (not shown). Bcl-2 protein levels were analyzed by Western blot analysis. As can be seen from FIGS. 8A-D Bcl-2 activation was most pronounced for the wild-type form, indicating that the examined tyrosines are important for Bcl-2 expression. The effect of CD84 ECD (as described below) on Bcl-2 expression is further shown in FIG. 8D.

To further follow the CD84 donwstream cascade TAp63 mRNA levels in HEK transfected cells were analyzed at different time points after transfection. As shown in FIG. 9, there was an increase in TAp63 mRNA expression in CD84-full transfected cells, compared to empty vector transfected cells, while the tyrosine mutations ablated this CD84 induced effect.

Example 5

Design, Expression and Purification of a Soluble CD84 Protein (CD84-ECD)

Beside selective activation of specific cell surface receptors, blocking of signaling is a desirable tool for studying the function of receptors, which have unknown function or unknown mechanisms of action.

Figure 10B:
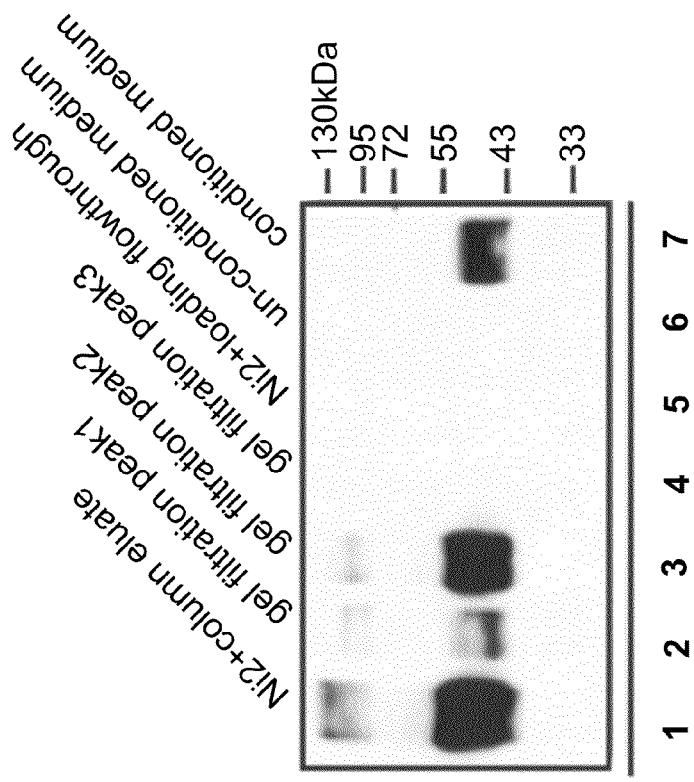
Figure 10A:
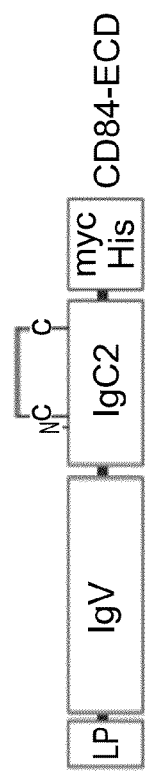
Figures 10C, 10D:
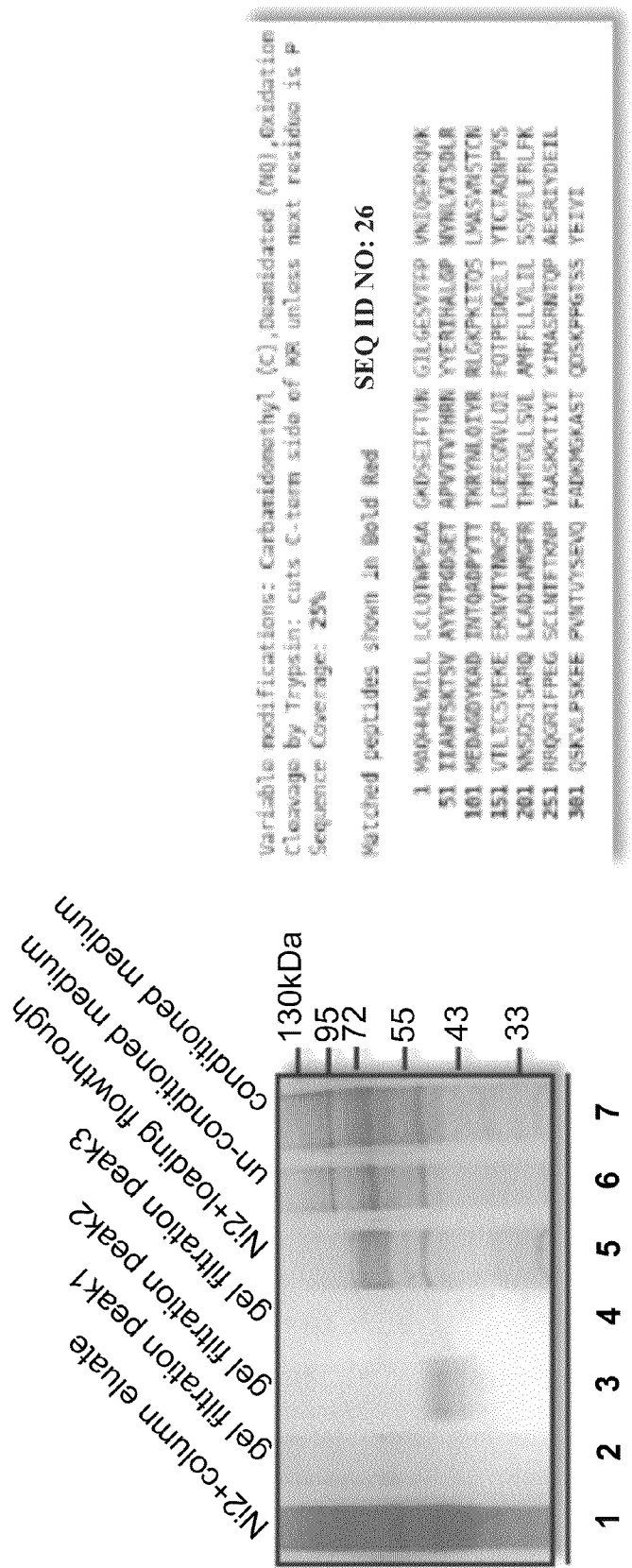

As CD84 is a self-ligand, expression of its extracellular domain can result in inhibition of cell-surface CD84 activation in a competitive manner. Therefore, a construct of myc/his6 tagged extracellular domain of CD84 (CD84-ECD) was generated (FIG. 10A). HEK 293T cells were transfected with the CD84-ECD construct and the cells' conditioned medium (CM) was collected. To prove the secretion of the protein, the CM was subjected to SDS-PAGE and Western blot analysis. Probing with anti-myc antibodies showed a prominent band between 43 kDa and 50 kDa (shown in FIG. 10B).

Recombinant CD84-ECD protein was purified from CM with a FLPC system. FIG. 11 shows the elution profile of the gel filtration chromatography with a calibrated Sephadex 200 column, followed by UV absorption. Three distinct peaks could be observed with retention times far above the expected size of monomeric CD84-ECD. Analysis of the eluted fractions of peak 1-3 and of the Ni2+ affinity chromatography samples by SDS-PAGE and Coomassie staining or Western blot confirmed that myc- and His6-tagged CD84-ECD protein was actually present in peak 1 and 2 (FIG. 10C) with the main amount in peak 2 at 65-75 mL elution volume. To verify the identity of the protein, the band of peak 2 was excised from the Comassie stained gel and was analyzed by proteolytic digestion followed by ESI-MS/MS (FIG. 10D). 18 protein fragments covering amino acids 51 to 220 could be detected.

In order to determine the yield of produced protein, the eluted peak 2 from the gel filtration was concentrated to a volume of 500 µl. For 100 ml medium or a cell culture surface area of 525 cm² the yield of protein was determined to be 50 µg, which is 1 µg/10 cm² (for 3 days of expression). In order to utilize the CD84-ECD as a competitive blocking molecule for CD84, HEK 293T cells were transfected with CD84-full and CD84-ECD and CD84-ECD effect on CD84 function was analyzed. As a first experiment, HEK 293T cells were transfected with equal amounts of total plasmid DNA of empty vector, CD84-full or CD84-full and CD84-ECD. The protein expression was verified by Western blot analysis with anti-myc antibody (FIG. 12A). Due to the different CD84-full plasmid DNA amounts, less CD84-full was expressed in the co-transfected cells. CD84-full-transfected cells showed an increase in Bcl-2 expression, compared to empty vector-transfected cells. This increase was abolished in cells co-transfected with CD84-ECD (FIG. 12A). As FIG. 12B shows, transfection with CD84-ECD alone had no significant effect on Bcl-2 expression levels. Since the different amounts of CD84-full might be responsible for the lower Bcl-2 expression in the co-transfected cells, a similar experiment with equal amounts of CD84-full plasmid DNA was performed with a similar outcome (FIG. 12c).

Another approach was to transfect the established CD84 cell lines with CD84-EDC. HEK 293T cells and the cell line CD84s20 were transfected with empty or CD84-ECD vectors. After 24 h the mRNA levels were analyzed by semiquantitative RT-PCR with Actin as a reference gene (FIG. 13). While HEK 293T cells showed no substantial change in Bcl-2 expression following CD84-ECD transfection, the stable cell line exhibited a remarkable decrease in both Bcl-2 and p63 mRNA levels.

To directly show the effect of CD84-ECD on CD84 induced survival cascade, conditioned medium derived from CD84-ECD transfect cells was collected (see FIG. 14). The CM was concentrated and diluted again in the cell culture medium to reach a final CD84-ECD concentration of 0.3 µg/ml, which was approximately the amount of CD84-ECD in the previous experiments or 3.75 µg/mL CD84-ECD (which should lead to CD84-cross-linking by high amounts of protein, adhered to surfaces). CD84-expressing cell line were incubated in the presence or absence of the low or high concentrated CM. As shown in FIG. 14 low levels of CD84-ECD inhibited the elevation of the Bcl-2 mRNA compared to empty vector transfected cells. Incubation with the high CD84-ECD concentration resulted in a dramatic Bcl-2 increase. Taken together these results, the extracellular domain of CD84 is a promising candidate for further research in order to find a blocking molecule for CD84.

Example 6

Anti CD84 Antibodies Which Can be Used as Neutralizing Antibodies or Activating Antibodies Hybrydoma Protocol CD84-ECD protein was purified from conditioned medium derived from 293 transfected with the CD84-ECD construct. Mice were injected for 5 months with CD84-ECD. Following positive ELISA test bleeding for antibodies against CD84-ECD, spleens were removed, lymphocytes were isolated and mixed with NSO cells. Hybridoma were selected and their sup were analyzed for recognition of CD84-ECD using ELISA assay.

To determine whether cell surface CD84 transmits a signal that results in activation of downstream signaling cascades in B-CLL cells, CD84 was cross-linked with anti-CD84 (Santa Cruz) or control IgG1 antibody mAb (Abcam) [Tangye, 2002]. The cells were then washed, and bound mAb was cross-linked with F(ab')2 goat anti-mouse Ig. CD84 tyrosine phosphorylation was first examined following ligation. As shown in FIG. 3A, CD84 activation induced phosphorylation of its cytoplasmic tail, indicating the initiation of a signaling cascade. Next the CD84 downstream cascade was examinrf, and especially its role in B-CLL survival. It was previously shown that stimulation of cell surface CD74 on B-CLL cells results in elevation of IL-8 and Bcl-2 expression [Binsky, 2007]. Therefore IL-8 and Bcl-2 mRNA levels were analyzed following CD84 stimulation. B-CLL were incubated in the presence or absence of anti-CD84, and mRNA levels of IL-8 and BCL-2 were analyzed. As shown in FIG. 3B, CD84 stimulation upregulated IL-8 and Bcl-2 mRNA levels, indicating that activation of B-CLL CD84 initiates a survival cascade.

To directly determine whether CD74 induces B-CLL survival in a CD84 dependent manner, CD84 activity was blocked using a commercially available CD84 blocking antibody (CD84.1.21 Biolegend) and the the MIF induced survival cascade was followed. Bcl-2 mRNA mRNA (FIG. 15A) and protein (FIG. 15B) levels were analyzed and cell survival was analyzed by FLICA staining (FIG. 15C). Blocking CD84 downregulated Bcl-2 expression and elevated cell death in MIF-treated cells, showing that CD84 is an essential component in the CD74-induced survival cascade.

To determine whether the monoclonal antibodies for CD84 transmit a signal that results in activation or inhibition of the CD84 downstream signaling cascades in B-CLL cells, CLL cells were treated with supernatant derived from hybridoma D1-300 and F8-500. 18 h later Bcl-2 mRNA levels were analyzed by Real time-PCR. As shown in FIGS. 16A-B, incubation with antibodies derived from D1-300 hybridoma resulted in upregulation of Bcl-2 mRNA levels (FIG. 16A) as well as reduces the apoptotic population (FIG. 16B), indicating that this hybridoma activates B-CLL CD84 survival cascade. However, incubation with antibodies derived from F8-500 hybridoma downregulated Bcl-2 mRNA levels (FIG. 16A) and induced cell death (FIG. 16B), indicating that this hybridoma inhibits CD84 signaling cascade. To further analyze the inhibitory effect of antibodies derived from hybridoma F8-500, B-CLL cells were treated with MIF together with the antibodies derived from hybridoma F8-500. The apoptotic population was then analyzed by magic red staining. As shown in FIG. 17, hybridoma F8-500 eliminated the MIF-induced survival cascade, indicating that CD84, is an essential component in the CD74-induced survival cascade and its blockage induces cell death.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of inducing apoptosis in B cells of a subject having B-CLL, the method comprising administering to the subject a therapeutically effective amount of an agent which downregulates an expression level and/or an activity of CD84, wherein said agent is selected from the group consisting of:
   (i) a CD84 neutralizing antibody;
   and
   (ii) a soluble CD84, wherein said soluble CD84 binds CD84 expressed on B cells and inhibits its homophilic interaction,
   thereby inducing apoptosis in B cells of the subject.

2. The method of claim 1, wherein said CD84 neutralizing antibody is an antibody having the CDR sequences of the anti-CD84 antibody produced by the hybridoma which has been deposited at the CNCM Pasteur Institute under the deposit number CNCM I-4228 (F8).

3. The method of claim 1, wherein said soluble CD84 comprises SEQ ID NO: 2, and wherein said soluble CD84 binds CD84 expressed on B cells and inhibits its homophilic interaction.

4. A method of treating B-CLL in a subject in need thereof, the method comprising administering to the subject a therapeutically effective amount of an agent which downregulates an expression level and/or an activity of CD84, wherein said agent is selected from the group consisting of:
   (i) a CD84 neutralizing antibody;
   and
   (ii) a soluble CD84, wherein said soluble CD84 binds CD84 expressed on B cells and inhibits its homophilic interaction,
   thereby treating B-CLL.

5. The method of claim 4, wherein said CD84 neutralizing antibody is an antibody having the CDR sequences of the anti-CD84 antibody produced by the hybridoma which has been deposited at the CNCM Pasteur Institute under the deposit number CNCM I-4228 (F8).

6. The method of claim 4, wherein said soluble CD84 comprises SEQ ID NO: 2, and wherein said soluble CD84 binds CD84 expressed on B cells and inhibits its homophilic interaction.

\* \* \* \* \*

SEQUENCE LISTING

<160> NUMBER OF SEQ ID NOS: 34

<210> SEQ ID NO 1
<211> LENGTH: 780
<212> TYPE: DNA
<213> ORGANISM: Artificial sequence
<220> FEATURE:
<223> OTHER INFORMATION: Soluble CD84 expressing polynucleotide

<400> SEQUENCE: 1

```
atggctcagc accacctatg gatcttgctc ctttgcctgc aaacctggcc ggaagcagct      60
ggaaaagact cagaaatctt cacagtgaat gggattctgg gagagtcagt cactttccct     120
gtaaatatcc aagaaccacg gcaagttaaa atcattgctt ggacttctaa acatctgtt     180
gcttatgtaa caccaggaga ctcagaaaca gcacccgtag ttactgtgac ccacagaaat     240
tattatgaac ggatacatgc cttaggtccg aactacaatc tggtcattag cgatctgagg     300
atggaagacg caggagacta caaagcagac ataaatacac aggctgatcc ctacaccacc     360
accaagcgct acaacctgca atctatcgt cggcttggga accaaaaat tacacagagt      420
ttaatggcat ctgtgaacag cacctgtaat gtcacactga catgctctgt agagaaagaa     480
gaaaagaatg tgacatacaa ttggagtccc ctgggagaag agggtaatgt ccttcaaatc     540
ttccagactc ctgaggacca agagctgact tacacgtgta cagcccagaa ccctgtcagc     600
aacaattctg actccatctc tgcccggcag ctctgtgcag acatcgcaat gggcttccgt     660
gaattctgca gatatccagc acagtggcgg ccgctcgagt ctagagggcc cttcgaacaa     720
aaactcatct cagaagagga tctgaatatg cataccggtc atcatcacca tcaccattga     780
```

<210> SEQ ID NO 2
<211> LENGTH: 239
<212> TYPE: PRT
<213> ORGANISM: Artificial sequence
<220> FEATURE:
<223> OTHER INFORMATION: Soluble CD84 polypeptide

<400> SEQUENCE: 2

```
Met Ala Gln His His Leu Trp Ile Leu Leu Leu Cys Leu Gln Thr Trp
1               5                   10                  15

Pro Glu Ala Ala Gly Lys Asp Ser Glu Ile Phe Thr Val Asn Gly Ile
            20                  25                  30

Leu Gly Glu Ser Val Thr Phe Pro Val Asn Ile Gln Glu Pro Arg Gln
        35                  40                  45

Val Lys Ile Ile Ala Trp Thr Ser Lys Thr Ser Val Ala Tyr Val Thr
    50                  55                  60

Pro Gly Asp Ser Glu Thr Ala Pro Val Val Thr Val Thr His Arg Asn
65                  70                  75                  80

Tyr Tyr Glu Arg Ile His Ala Leu Gly Pro Asn Tyr Asn Leu Val Ile
                85                  90                  95

Ser Asp Leu Arg Met Glu Asp Ala Gly Asp Tyr Lys Ala Asp Ile Asn
            100                 105                 110

Thr Gln Ala Asp Pro Tyr Thr Thr Leu Met Ala Ser Val Asn Ser Thr
        115                 120                 125

Cys Asn Val Thr Leu Thr Cys Ser Val Glu Lys Glu Glu Lys Asn Val
    130                 135                 140

Thr Tyr Asn Trp Ser Pro Leu Gly Glu Glu Gly Asn Val Leu Gln Ile
145                 150                 155                 160

Phe Gln Thr Pro Glu Asp Gln Glu Leu Thr Tyr Thr Cys Thr Ala Gln
```

```
                    165                 170                 175
Asn Pro Val Ser Asn Asn Ser Asp Ser Ile Ser Ala Arg Gln Leu Cys
            180                 185                 190

Ala Asp Ile Ala Met Gly Phe Arg Glu Phe Cys Arg Tyr Pro Ala Gln
        195                 200                 205

Trp Arg Pro Leu Glu Ser Arg Gly Pro Phe Glu Gln Lys Leu Ile Ser
    210                 215                 220

Glu Glu Asp Leu Asn Met His Thr Gly His His His His His His
225                 230                 235

<210> SEQ ID NO 3
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 3
tacatgcctt aggtccga                                                    18

<210> SEQ ID NO 4
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 4
gagggaagca ccttgt                                                      16

<210> SEQ ID NO 5
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 5
tgcctgcaaa cctggccgga agca                                             24

<210> SEQ ID NO 6
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 6
tgcaggttgt agcgcttggt ggtggt                                           26

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
agcgtgccag gcgtgtactg                                                  20

<210> SEQ ID NO 8
<211> LENGTH: 21
<212> TYPE: DNA
<213> ORGANISM: Artificial sequence
```

```
<220> FEATURE:
<223> OTHER INFORMATION: Single strand DNA oligonucleotide

<400> SEQUENCE: 8
acaccagcca acttcccacc a                                              21

<210> SEQ ID NO 9
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 9
gctcaaggaa ggggtggatg gc                                             22

<210> SEQ ID NO 10
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 10
tctggtgctg gtgggcagaa c                                              21

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
acaagtgaag tcaacatgcc                                                20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
gcaagtgaat gaacaccttc                                                20

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
tgaagtgtga cgtggacatc cg                                             22

<210> SEQ ID NO 14
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 14
gctgtcacct tcaccgttcc ag                                             22
```

<210> SEQ ID NO 15
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 15
gatgctgcct caaagaaaac catattcaca tatatcatgg cttc                          44

<210> SEQ ID NO 16
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 16
gaagccatga tatatgtgaa tatggttttc tttgaggcag catc                          44

<210> SEQ ID NO 17
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 17
gagccagtga acacagtttt ttccgaagtg cagt                                     34

<210> SEQ ID NO 18
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 18
actgcacttc ggaaaaaact gtgttcactg gctc                                     34

<210> SEQ ID NO 19
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 19
gccagcagag tccagaatct ttgatgaaat cctg                                     34

<210> SEQ ID NO 20
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 20
caggatttca tcaaagattc tggactctgc tggc                                     34

<210> SEQ ID NO 21
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 21
acctcctggg acttcaagct ttgaaattgt gatcg            35

<210> SEQ ID NO 22
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 22
cgatcacaat ttcaaagctt gaagtcccag gaggt            35

<210> SEQ ID NO 23
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 23
cgtcggatcc atggctcagc accac                       25

<210> SEQ ID NO 24
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 24
tagcgaattc acggaagccc attgc                       25

<210> SEQ ID NO 25
<211> LENGTH: 1118
<212> TYPE: DNA
<213> ORGANISM: Homo sapiens

<400> SEQUENCE: 25
cggctcaagt gaactgactc tgctagaaca gtgccgtgct tttccacaga aggttagacc     60
ctgaaagaga tggctcagca ccacctatgg atcttgctcc tttgcctgca aacctggccg    120
gaagcagctg gaaaagactc agaaatcttc acagtgaatg ggattctggg agagtcagtc    180
actttccctg taaatatcca agaaccacgg caagttaaaa tcattgcttg gacttctaaa    240
acatctgttg cttatgtaac accaggagac tcagaaacag cacccgtagt tactgtgacc    300
cacagaaatt attatgaacg gatacatgcc ttaggtccga actacaatct ggtcattagc    360
gatctgagga tggaagacgc aggagactac aaagcagaca taaatacaca ggctgatccc    420
tacaccacca ccaagcgcta caacctgcaa atctatcgtc ggcttgggaa accaaaaatt    480
acacagagtt aatggcatc tgtgaacagc acctgtaatg tcacactgac atgctctgta    540
gagaaagaag aaaagaatgt gacatacaat tggagtcccc tgggagaaga gggtaatgtc    600
cttcaaatct tccagactcc tgaggaccaa gagctgactt acacgtgtac agcccagaac    660
cctgtcagca caattctga ctccatctct gcccggcagc tctgtgcaga catcgcaatg    720
ggcttccgta ctcaccacac cgggttgctg agcgtgctgg ctatgttctt tctgcttgtt    780
ctcattctgt cttcagtgtt tttgttccgt tgttcaaga gaagacaagg taggattttc    840
ccagaaggtt cctgcttgaa caccttcact aagaaccctt atgctgcctc aaagaaaacc    900

```
atatacacat atatcatggc ttcaaggaac acccagccag cagagtccag aatctatgat      960
gaaatcctgc agtccaaggt gcttccctcc aaggaagagc cagtgaacac agtttattcc     1020
gaagtgcagt ttgctgataa gatggggaaa gccagcacac aggacagtaa acctcctggg     1080
acttcaagct atgaaattgt gatctaggct gctgggct                             1118
```

<210> SEQ ID NO 26
<211> LENGTH: 345
<212> TYPE: PRT
<213> ORGANISM: Homo sapiens

<400> SEQUENCE: 26

```
Met Ala Gln His His Leu Trp Ile Leu Leu Cys Leu Gln Thr Trp
1               5                   10                  15

Pro Glu Ala Ala Gly Lys Asp Ser Glu Ile Phe Thr Val Asn Gly Ile
                20                  25                  30

Leu Gly Glu Ser Val Thr Phe Pro Val Asn Ile Gln Glu Pro Arg Gln
            35                  40                  45

Val Lys Ile Ile Ala Trp Thr Ser Lys Thr Ser Val Ala Tyr Val Thr
        50                  55                  60

Pro Gly Asp Ser Glu Thr Ala Pro Val Val Thr Val Thr His Arg Asn
65                  70                  75                  80

Tyr Tyr Glu Arg Ile His Ala Leu Gly Pro Asn Tyr Asn Leu Val Ile
                85                  90                  95

Ser Asp Leu Arg Met Glu Asp Ala Gly Asp Tyr Lys Ala Asp Ile Asn
            100                 105                 110

Thr Gln Ala Asp Pro Tyr Thr Thr Thr Lys Arg Tyr Asn Leu Gln Ile
        115                 120                 125

Tyr Arg Arg Leu Gly Lys Pro Lys Ile Thr Gln Ser Leu Met Ala Ser
    130                 135                 140

Val Asn Ser Thr Cys Asn Val Thr Leu Thr Cys Ser Val Glu Lys Glu
145                 150                 155                 160

Glu Lys Asn Val Thr Tyr Asn Trp Ser Pro Leu Gly Glu Glu Gly Asn
                165                 170                 175

Val Leu Gln Ile Phe Gln Thr Pro Glu Asp Gln Glu Leu Thr Tyr Thr
            180                 185                 190

Cys Thr Ala Gln Asn Pro Val Ser Asn Asn Ser Asp Ser Ile Ser Ala
        195                 200                 205

Arg Gln Leu Cys Ala Asp Ile Ala Met Gly Phe Arg Thr His His Thr
    210                 215                 220

Gly Leu Leu Ser Val Leu Ala Met Phe Phe Leu Val Leu Ile Leu
225                 230                 235                 240

Ser Ser Val Phe Leu Phe Arg Leu Phe Lys Arg Arg Gln Gly Arg Ile
                245                 250                 255

Phe Pro Glu Gly Ser Cys Leu Asn Thr Phe Thr Lys Asn Pro Tyr Ala
            260                 265                 270

Ala Ser Lys Lys Thr Ile Tyr Thr Tyr Ile Met Ala Ser Arg Asn Thr
        275                 280                 285

Gln Pro Ala Glu Ser Arg Ile Tyr Asp Glu Ile Leu Gln Ser Lys Val
    290                 295                 300

Leu Pro Ser Lys Glu Glu Pro Val Asn Thr Val Tyr Ser Glu Val Gln
305                 310                 315                 320

Phe Ala Asp Lys Met Gly Lys Ala Ser Thr Gln Asp Ser Lys Pro Pro
                325                 330                 335
```

Gly Thr Ser Ser Tyr Glu Ile Val Ile
            340                 345

<210> SEQ ID NO 27
<211> LENGTH: 1100
<212> TYPE: DNA
<213> ORGANISM: Homo sapiens

<400> SEQUENCE: 27

| | | | | | |
|---|---|---|---|---|---|
| cggctcaagt | gaactgactc | tgctagaaca | gtgccgtgct | tttccacaga | aggttagacc | 60 |
| ctgaaagaga | tggctcagca | ccacctatgg | atcttgctcc | tttgcctgca | aacctggccg | 120 |
| gaagcagctg | gaaaagactc | agaaatcttc | acagtgaatg | ggattctggg | agagtcagtc | 180 |
| actttccctg | taaatatcca | agaaccacgg | caagttaaaa | tcattgcttg | gacttctaaa | 240 |
| acatctgttg | cttatgtaac | accaggagac | tcagaaacag | cacccgtagt | tactgtgacc | 300 |
| cacagaaatt | attatgaacg | gatacatgcc | ttaggtccga | actacaatct | ggtcattagc | 360 |
| gatctgagga | tggaagacgc | aggagactac | aaagcagaca | taaatacaca | ggctgatccc | 420 |
| tacaccacca | ccaagcgcta | caacctgcaa | atctatcgtc | ggcttgggaa | accaaaaatt | 480 |
| acacagagtt | taatggcatc | tgtgaacagc | acctgtaatg | tcacactgac | atgctctgta | 540 |
| gagaaagaag | aaaagaatgt | gacatacaat | tggagtcccc | tgggagaaga | gggtaatgtc | 600 |
| cttcaaatct | tccagactcc | tgaggaccaa | gagctgactt | acacgtgtac | agcccagaac | 660 |
| cctgtcagca | acaattctga | ctccatctct | gcccggcagc | tctgtgcaga | catcgcaatg | 720 |
| ggcttccgta | ctcaccacac | cgggttgctg | agcgtgctgg | ctatgttctt | tctgcttgtt | 780 |
| ctcattctgt | cttcagtgtt | tttgttccgt | tgttcaaga | aagacaagg | ttcctgcttg | 840 |
| aacaccttca | ctaagaaccc | ttatgctgcc | tcaaagaaaa | ccatatacac | atatatcatg | 900 |
| gcttcaagga | acacccagcc | agcagagtcc | agaatctatg | atgaaatcct | gcagtccaag | 960 |
| gtgcttccct | ccaaggaaga | gccagtgaac | acagtttatt | ccgaagtgca | gtttgctgat | 1020 |
| aagatgggga | aagccagcac | acaggacagt | aaacctcctg | ggacttcaag | ctatgaaatt | 1080 |
| gtgatctagg | ctgctgggct | | | | | 1100 |

<210> SEQ ID NO 28
<211> LENGTH: 339
<212> TYPE: PRT
<213> ORGANISM: Homo sapiens

<400> SEQUENCE: 28

Met Ala Gln His His Leu Trp Ile Leu Leu Cys Leu Gln Thr Trp
1               5                   10                  15

Pro Glu Ala Ala Gly Lys Asp Ser Glu Ile Phe Thr Val Asn Gly Ile
                20                  25                  30

Leu Gly Glu Ser Val Thr Phe Pro Val Asn Ile Gln Glu Pro Arg Gln
            35                  40                  45

Val Lys Ile Ile Ala Trp Thr Ser Lys Thr Ser Val Ala Tyr Val Thr
        50                  55                  60

Pro Gly Asp Ser Glu Thr Ala Pro Val Val Thr Val Thr His Arg Asn
65                  70                  75                  80

Tyr Tyr Glu Arg Ile His Ala Leu Gly Pro Asn Tyr Asn Leu Val Ile
                85                  90                  95

Ser Asp Leu Arg Met Glu Asp Ala Gly Asp Tyr Lys Ala Asp Ile Asn
            100                 105                 110

Thr Gln Ala Asp Pro Tyr Thr Thr Thr Lys Arg Tyr Asn Leu Gln Ile

|  | 115 |  |  |  | 120 |  |  |  | 125 |  |  |
|---|---|---|---|---|---|---|---|---|---|---|---|

Tyr Arg Arg Leu Gly Lys Pro Lys Ile Thr Gln Ser Leu Met Ala Ser
             130                    135                  140

Val Asn Ser Thr Cys Asn Val Thr Leu Thr Cys Ser Val Glu Lys Glu
145                   150                    155                  160

Glu Lys Asn Val Thr Tyr Asn Trp Ser Pro Leu Gly Glu Glu Gly Asn
                  165                    170                  175

Val Leu Gln Ile Phe Gln Thr Pro Glu Asp Gln Glu Leu Thr Tyr Thr
             180                    185                  190

Cys Thr Ala Gln Asn Pro Val Ser Asn Asn Ser Asp Ser Ile Ser Ala
                  195                    200                205

Arg Gln Leu Cys Ala Asp Ile Ala Met Gly Phe Arg Thr His His Thr
             210                    215                220

Gly Leu Leu Ser Val Leu Ala Met Phe Phe Leu Leu Val Leu Ile Leu
225                   230                    235                240

Ser Ser Val Phe Leu Phe Arg Leu Phe Lys Arg Arg Gln Gly Ser Cys
                  245                    250                255

Leu Asn Thr Phe Thr Lys Asn Pro Tyr Ala Ala Ser Lys Lys Thr Ile
             260                    265                270

Tyr Thr Tyr Ile Met Ala Ser Arg Asn Thr Gln Pro Ala Glu Ser Arg
                  275                    280                285

Ile Tyr Asp Glu Ile Leu Gln Ser Lys Val Leu Pro Ser Lys Glu Glu
             290                    295                300

Pro Val Asn Thr Val Tyr Ser Glu Val Gln Phe Ala Asp Lys Met Gly
305                   310                    315                320

Lys Ala Ser Thr Gln Asp Ser Lys Pro Pro Gly Thr Ser Ser Tyr Glu
                  325                    330                335

Ile Val Ile

<210> SEQ ID NO 29
<211> LENGTH: 1067
<212> TYPE: DNA
<213> ORGANISM: Homo sapiens

<400> SEQUENCE: 29

| cggctcaagt | gaactgactc | tgctagaaca | gtgccgtgct | tttccacaga | aggttagacc | 60 |
| ctgaaagaga | tggctcagca | ccacctatgg | atcttgctcc | tttgcctgca | aacctggccg | 120 |
| gaagcagctg | gaaagactc | agaaatcttc | acagtgaatg | ggattctggg | agagtcagtc | 180 |
| actttccctg | taaatatcca | agaaccacgg | caagttaaaa | tcattgcttg | gacttctaaa | 240 |
| acatctgttg | cttatgtaac | accaggagac | tcagaaacag | caccgtagt | tactgtgacc | 300 |
| cacagaaatt | attatgaacg | gatacatgcc | ttaggtccga | actacaatct | ggtcattagc | 360 |
| gatctgagga | tggaagacgc | aggagactac | aaagcagaca | taaatacaca | ggctgatccc | 420 |
| tacaccacca | ccaagcgcta | caacctgcaa | atctatcgtc | ggcttgggaa | accaaaaatt | 480 |
| acacagagtt | taatggcatc | tgtgaacagc | acctgtaatg | tcacactgac | atgctctgta | 540 |
| gagaaagaag | aaaagaatgt | gacatacaat | tggagtcccc | tgggagaaga | gggtaatgtc | 600 |
| cttcaaatct | tccagactcc | tgaggaccaa | gagctgactt | acacgtgtac | agcccagaac | 660 |
| cctgtcagca | acaattctga | ctccatctct | gcccggcagc | tctgtgcaga | catcgcaatg | 720 |
| ggcttccgta | ctcaccacac | cgggttgctg | agcgtgctgg | ctatgttctt | tctgcttgtt | 780 |
| ctcattctgt | cttcagtgtt | tttgttccgt | ttgttcaaga | gaagacaaga | tgctgcctca | 840 |

```
aagaaaacca tatacacata tatcatggct tcaaggaaca cccagccagc agagtccaga    900
atctatgatg aaatcctgca gtccaaggtg cttccctcca aggaagagcc agtgaacaca    960
gtttattccg aagtgcagtt tgctgataag atggggaaag ccagcacaca ggacagtaaa   1020
cctcctggga cttcaagcta tgaaattgtg atctaggctg ctgggct                 1067
```

<210> SEQ ID NO 30
<211> LENGTH: 328
<212> TYPE: PRT
<213> ORGANISM: Homo sapiens

<400> SEQUENCE: 30

```
Met Ala Gln His His Leu Trp Ile Leu Leu Cys Leu Gln Thr Trp
1               5                   10                  15

Pro Glu Ala Ala Gly Lys Asp Ser Glu Ile Phe Thr Val Asn Gly Ile
        20                  25                  30

Leu Gly Glu Ser Val Thr Phe Pro Val Asn Ile Gln Glu Pro Arg Gln
    35                  40                  45

Val Lys Ile Ile Ala Trp Thr Ser Lys Thr Ser Val Ala Tyr Val Thr
50                  55                  60

Pro Gly Asp Ser Glu Thr Ala Pro Val Val Thr Val Thr His Arg Asn
65                  70                  75                  80

Tyr Tyr Glu Arg Ile His Ala Leu Gly Pro Asn Tyr Asn Leu Val Ile
                85                  90                  95

Ser Asp Leu Arg Met Glu Asp Ala Gly Asp Tyr Lys Ala Asp Ile Asn
            100                 105                 110

Thr Gln Ala Asp Pro Tyr Thr Thr Thr Lys Arg Tyr Asn Leu Gln Ile
        115                 120                 125

Tyr Arg Arg Leu Gly Lys Pro Lys Ile Thr Gln Ser Leu Met Ala Ser
    130                 135                 140

Val Asn Ser Thr Cys Asn Val Thr Leu Thr Cys Ser Val Glu Lys Glu
145                 150                 155                 160

Glu Lys Asn Val Thr Tyr Asn Trp Ser Pro Leu Gly Glu Glu Gly Asn
                165                 170                 175

Val Leu Gln Ile Phe Gln Thr Pro Glu Asp Gln Glu Leu Thr Tyr Thr
            180                 185                 190

Cys Thr Ala Gln Asn Pro Val Ser Asn Asn Ser Asp Ser Ile Ser Ala
        195                 200                 205

Arg Gln Leu Cys Ala Asp Ile Ala Met Gly Phe Arg Thr His His Thr
    210                 215                 220

Gly Leu Leu Ser Val Leu Ala Met Phe Phe Leu Val Leu Ile Leu
225                 230                 235                 240

Ser Ser Val Phe Leu Phe Arg Leu Phe Lys Arg Arg Gln Asp Ala Ala
                245                 250                 255

Ser Lys Lys Thr Ile Tyr Thr Tyr Ile Met Ala Ser Arg Asn Thr Gln
            260                 265                 270

Pro Ala Glu Ser Arg Ile Tyr Asp Glu Ile Leu Gln Ser Lys Val Leu
        275                 280                 285

Pro Ser Lys Glu Glu Pro Val Asn Thr Val Tyr Ser Glu Val Gln Phe
    290                 295                 300

Ala Asp Lys Met Gly Lys Ala Ser Thr Gln Asp Ser Lys Pro Pro Gly
305                 310                 315                 320

Thr Ser Ser Tyr Glu Ile Val Ile
                325
```

<210> SEQ ID NO 31
<211> LENGTH: 967
<212> TYPE: DNA
<213> ORGANISM: Homo sapiens

<400> SEQUENCE: 31

```
cggctcaagt gaactgactc tgctagaaca gtgccgtgct tttccacaga aggttagacc      60
ctgaaagaga tggctcagca ccacctatgg atcttgctcc tttgcctgca aacctggccg     120
gaagcagctg gaaaagactc agaaatcttc acagtgaatg ggattctggg agagtcagtc     180
actttccctg taaatatcca gaaccacgg caagttaaaa tcattgcttg gacttctaaa      240
acatctgttg cttatgtaac accaggagac tcagaaacag cacccgtagt tactgtgacc     300
cacagaaatt attatgaacg gatacatgcc ttaggtccga actacaatct ggtcattagc     360
gatctgagga tggaagacgc aggagactac aaagcagaca taaatacaca ggctgatccc     420
tacaccacca ccaagcgcta caacctgcaa atctatcgtc ggcttgggaa accaaaaatt     480
acacagagtt aatggcatc tgtgaacagc acctgtaatg tcacactgac atgctctgta     540
gagaaagaag aaaagaatgt gacatacaat tggagtcccc tgggagaaga gggtaatgtc     600
cttcaaatct tccagactcc tgaggaccaa gagctgactt acacgtgtac agcccagaac     660
cctgtcagca caattctga ctccatctct gcccggcagc tctgtgcaga catcgcaatg     720
ggcttccgta ctcaccacac cgggttgctg agcgtgctgg ctatgttctt tctgcttgtt     780
ctcattctgt cttcagtgtt tttgttccgt tgttcaaga aagacaaggt gcttccctc      840
caaggaagag ccagtgaaca cagtttattc cgaagtgcag tttgctgata agatggggaa     900
agccagcaca caggacagta aacctcctgg gacttcaagc tatgaaattg tgatctaggc     960
tgctggg                                                                967
```

<210> SEQ ID NO 32
<211> LENGTH: 272
<212> TYPE: PRT
<213> ORGANISM: Homo sapiens

<400> SEQUENCE: 32

```
Met Ala Gln His His Leu Trp Ile Leu Leu Leu Cys Leu Gln Thr Trp
1               5                   10                  15

Pro Glu Ala Ala Gly Lys Asp Ser Glu Ile Phe Thr Val Asn Gly Ile
            20                  25                  30

Leu Gly Glu Ser Val Thr Phe Pro Val Asn Ile Gln Glu Pro Arg Gln
        35                  40                  45

Val Lys Ile Ile Ala Trp Thr Ser Lys Thr Ser Val Ala Tyr Val Thr
    50                  55                  60

Pro Gly Asp Ser Glu Thr Ala Pro Val Val Thr Val Thr His Arg Asn
65                  70                  75                  80

Tyr Tyr Glu Arg Ile His Ala Leu Gly Pro Asn Tyr Asn Leu Val Ile
                85                  90                  95

Ser Asp Leu Arg Met Glu Asp Ala Gly Asp Tyr Lys Ala Asp Ile Asn
            100                 105                 110

Thr Gln Ala Asp Pro Tyr Thr Thr Thr Lys Arg Tyr Asn Leu Gln Ile
        115                 120                 125

Tyr Arg Arg Leu Gly Lys Pro Lys Ile Thr Gln Ser Leu Met Ala Ser
    130                 135                 140

Val Asn Ser Thr Cys Asn Val Thr Leu Thr Cys Ser Val Glu Lys Glu
145                 150                 155                 160
```

```
Glu Lys Asn Val Thr Tyr Asn Trp Ser Pro Leu Gly Glu Gly Asn
                165                 170                 175
Val Leu Gln Ile Phe Gln Thr Pro Glu Asp Gln Leu Thr Tyr Thr
                180                 185                 190
Cys Thr Ala Gln Asn Pro Val Ser Asn Asn Ser Asp Ser Ile Ser Ala
            195                 200                 205
Arg Gln Leu Cys Ala Asp Ile Ala Met Gly Phe Arg Thr His His Thr
            210                 215                 220
Gly Leu Leu Ser Val Leu Ala Met Phe Phe Leu Val Leu Ile Leu
225                 230                 235                 240
Ser Ser Val Phe Leu Phe Arg Leu Phe Lys Arg Gln Gly Ala Ser
                245                 250                 255
Leu Gln Gly Arg Ala Ser Glu His Ser Leu Phe Arg Ser Ala Val Cys
            260                 265                 270
```

<210> SEQ ID NO 33
<211> LENGTH: 1299
<212> TYPE: DNA
<213> ORGANISM: Homo sapiens

<400> SEQUENCE: 33

```
cggctcaagt gaactgactc tgctagaaca gtgccgtgct tttccacaga aggttagacc      60
ctgaaagaga tggctcagca ccacctatgg atcttgctcc tttgcctgca aacctggccg     120
gaagcagctg gaaaagactc agaaatcttc acagtgaatg ggattctggg agagtcagtc     180
actttccctg taaatatcca agaaccacgg caagttaaaa tcattgcttg gacttctaaa     240
acatctgttg cttatgtaac accaggagac tcagaaacag caccgtagt tactgtgacc     300
cacagaaatt attatgaacg gatacatgcc ttaggtccga actacaatct ggtcattagc     360
gatctgagga tggaagacgc aggagactac aaagcagaca taaatacaca ggctgatccc     420
tacaccacca ccaagcgcta caacctgcaa atctatcgtc ggcttgggaa ccaaaaaatt     480
acacagagtt taatggcatc tgtgaacagc acctgtaatg tcacactgac atgctctgta     540
gagaaagaag aaaagaatgt gacatacaat tggagtcccc tgggagaaga gggtaatgtc     600
cttcaaatct tccagactcc tgaggaccaa gagctgactt acacgtgtac agcccagaac     660
cctgtcagca caattctgac tccatctct gcccggcagc tctgtgcaga catcgcaatg     720
ggcttccgta ctcaccacac cgggttgctg agcgtgctgg ctatgttctt tctgcttgtt     780
ctcattctgt cttcagtgtt tttgttccgt ttgttcaaga agacaagg taggattttc     840
ccagaaggta aaatgtggaa actcaccttc tctcctcctg ggactgaagc catttatcca     900
aggtttagct gaaaggccca ttgttccagg aatctgcct ttttccgatc tccacccac      960
cacctcccag aatgatggct ctgaggatgg tatgacatta ccctgaatgg tcttcagaat    1020
ccattcctga tcaccagt agctggtggg cccagaacat gggttcgagc ttagtacata    1080
catgaacaag ctgtgcttca ctgtacgagt gtgttcacct ttccgctcag ggccctcaca    1140
tgtgaaatgt ttggactaga ggatctccag ggtcacttcc aatttcattg tattttgatt    1200
atgactattg gagagtcatt gagaaacata tactaatcct gtactccatg gttgtcacta    1260
tgtccctctg aatccctctg gatcattctg tagttgtgc                            1299
```

<210> SEQ ID NO 34
<211> LENGTH: 280
<212> TYPE: PRT
<213> ORGANISM: Homo sapiens -continued

```
<400> SEQUENCE: 34

Met Ala Gln His His Leu Trp Ile Leu Leu Cys Leu Gln Thr Trp
1               5                   10                  15

Pro Glu Ala Ala Gly Lys Asp Ser Glu Ile Phe Thr Val Asn Gly Ile
                20                  25                  30

Leu Gly Glu Ser Val Thr Phe Pro Val Asn Ile Gln Glu Pro Arg Gln
                35                  40                  45

Val Lys Ile Ile Ala Trp Thr Ser Lys Thr Ser Val Ala Tyr Val Thr
        50                  55                  60

Pro Gly Asp Ser Glu Thr Ala Pro Val Val Thr Val Thr His Arg Asn
65                  70                  75                  80

Tyr Tyr Glu Arg Ile His Ala Leu Gly Pro Asn Tyr Asn Leu Val Ile
                85                  90                  95

Ser Asp Leu Arg Met Glu Asp Ala Gly Asp Tyr Lys Ala Asp Ile Asn
                100                 105                 110

Thr Gln Ala Asp Pro Tyr Thr Thr Thr Lys Arg Tyr Asn Leu Gln Ile
                115                 120                 125

Tyr Arg Arg Leu Gly Lys Pro Lys Ile Thr Gln Ser Leu Met Ala Ser
        130                 135                 140

Val Asn Ser Thr Cys Asn Val Thr Leu Thr Cys Ser Val Glu Lys Glu
145                 150                 155                 160

Glu Lys Asn Val Thr Tyr Asn Trp Ser Pro Leu Gly Glu Glu Gly Asn
                165                 170                 175

Val Leu Gln Ile Phe Gln Thr Pro Glu Asp Gln Glu Leu Thr Tyr Thr
                180                 185                 190

Cys Thr Ala Gln Asn Pro Val Ser Asn Asn Ser Asp Ser Ile Ser Ala
                195                 200                 205

Arg Gln Leu Cys Ala Asp Ile Ala Met Gly Phe Arg Thr His His Thr
        210                 215                 220

Gly Leu Leu Ser Val Leu Ala Met Phe Phe Leu Leu Val Leu Ile Leu
225                 230                 235                 240

Ser Ser Val Phe Leu Phe Arg Leu Phe Lys Arg Arg Gln Gly Arg Ile
                245                 250                 255

Phe Pro Glu Gly Lys Met Trp Lys Leu Thr Phe Ser Pro Pro Gly Thr
                260                 265                 270

Glu Ala Ile Tyr Pro Arg Phe Ser
        275                 280
```